(12) United States Patent
Tanaka et al.

(10) Patent No.: US 11,707,316 B2
(45) Date of Patent: Jul. 25, 2023

(54) TREATMENT INSTRUMENT

(71) Applicant: OLYMPUS CORPORATION, Hachioji (JP)

(72) Inventors: Kazuhiro Tanaka, Hachioji (JP); Yuki Kawaguchi, Koshu (JP); Yusuke Takei, Hino (JP); Ojiro Kitamura, Hachioji (JP); Akinori Kobayashi, Hino (JP); Tomoyuki Takashino, Fuchu (JP); Tatsuro Yamamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1163 days.

(21) Appl. No.: 16/227,269

(22) Filed: Dec. 20, 2018

(65) Prior Publication Data

US 2019/0175257 A1 Jun. 13, 2019

Related U.S. Application Data

(63) Continuation of application No. PCT/JP2016/068287, filed on Jun. 20, 2016.

(51) Int. Cl.
*A61B 18/14* (2006.01)
*A61B 18/00* (2006.01)
(Continued)

(52) U.S. Cl.
CPC ...... *A61B 18/1445* (2013.01); *A61B 17/2909* (2013.01); *A61B 17/320092* (2013.01);
(Continued)

(58) Field of Classification Search
CPC .... A61B 2017/2927; A61B 2017/2946; A61B 2017/2929; A61B 2017/0046;
(Continued)

(56) References Cited

U.S. PATENT DOCUMENTS 5,383,888 A 1/1995 Zvenyatsky et al.
2007/0287993 A1* 12/2007 Hinman ................. A61B 17/29
606/1
(Continued)

FOREIGN PATENT DOCUMENTS

JP 2011-92743 A 5/2011
JP 2013-176651 A 9/2013

OTHER PUBLICATIONS

Aug. 30, 2016 International Search Report issued in International Patent Application No. PCT/JP2016/068287.
(Continued)

*Primary Examiner* — Khadijeh A Vahdat
*Assistant Examiner* — Mystee Nguyen Delgado
(74) *Attorney, Agent, or Firm* — Oliff PLC

(57) ABSTRACT

A treatment instrument includes a rotating body and a housing. The rotating body includes a connecting portion including: a supported portion having a cylindrical outer peripheral surface, and an engaged portion that is adjacent to the supported surface. The housing includes a supporting portion that is configured to support the supported portion of the rotating body, the supporting portion being rotatable around a predetermined rotation axis; and an engaging portion that is configured to generate a frictional force larger than a frictional force between the supporting portion and the supported portion by coming into contact with the engaged portion.

18 Claims, 16 Drawing Sheets

(51) Int. Cl.
*A61B 17/00* (2006.01)
*A61B 17/32* (2006.01)
*A61B 18/08* (2006.01)
*A61B 17/29* (2006.01)

(52) U.S. Cl.
CPC .. *A61B 18/085* (2013.01); *A61B 2017/00845* (2013.01); *A61B 2017/00858* (2013.01); *A61B 2017/2901* (2013.01); *A61B 2017/291* (2013.01); *A61B 2017/2912* (2013.01); *A61B 2017/2927* (2013.01); *A61B 2017/2929* (2013.01); *A61B 2018/00202* (2013.01)

(58) Field of Classification Search
CPC ...... A61B 2017/2905; A61B 17/00234; A61B 2017/00292; A61B 2017/00389; A61B 2017/00367; A61B 2017/0042; A61B 17/28; A61B 17/2909; A61B 18/00; A61B 18/1445; A61B 17/320092; A61B 18/085; A61B 2017/00845; A61B 2017/00858; A61B 2017/2901; A61B 2017/291; A61B 2017/2912; A61B 2018/00202; A61M 25/0147; A61M 25/0105; A61M 25/0133; A61F 2/9517

See application file for complete search history.

(56) References Cited

U.S. PATENT DOCUMENTS

| | | | | |
|---|---|---|---|---|
| 2011/0106073 | A1* | 5/2011 | Mueller | A61B 34/71 606/41 |
| 2013/0066303 | A1* | 3/2013 | Hart | A61B 17/29 606/1 |
| 2016/0302840 | A1* | 10/2016 | Scheib | A61B 18/00 |
| 2016/0327200 | A1* | 11/2016 | Crooks | F16M 11/08 |
| 2017/0112488 | A1* | 4/2017 | Baxter, III | A61B 17/0469 |

OTHER PUBLICATIONS

Nov. 26, 2020 Office Action issued in Japanese Patent Application No. 201680086967.3.
Nov. 26, 2020 Office Action issued in Chinese Patent Application No. 201680086967.3.

* cited by examiner

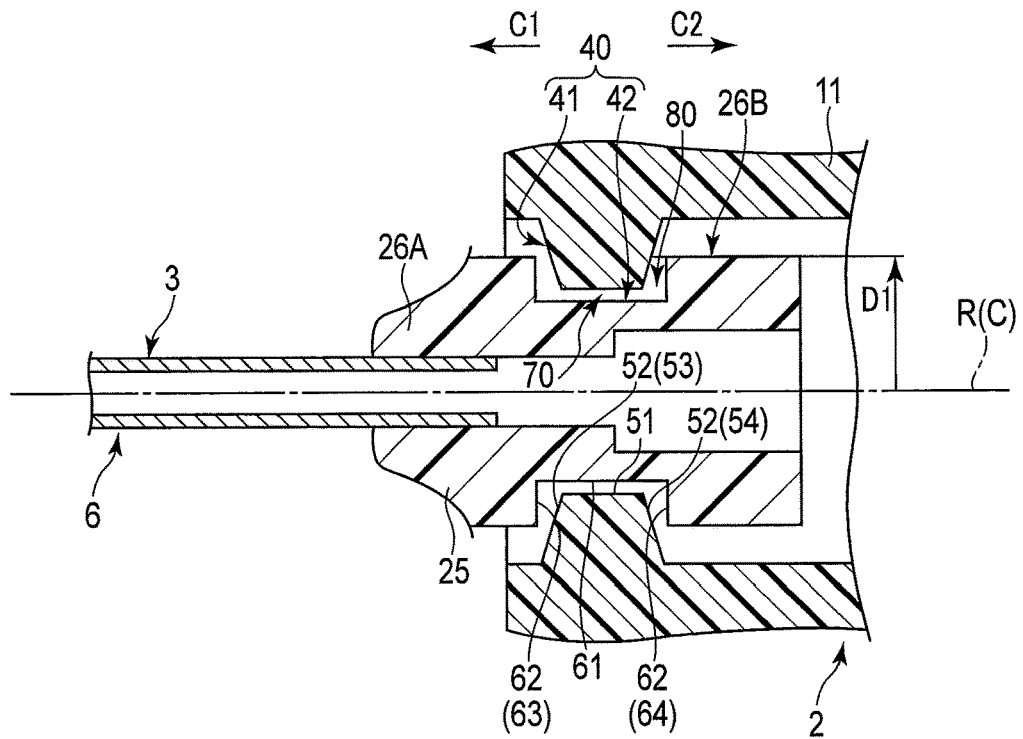
F I G. 4
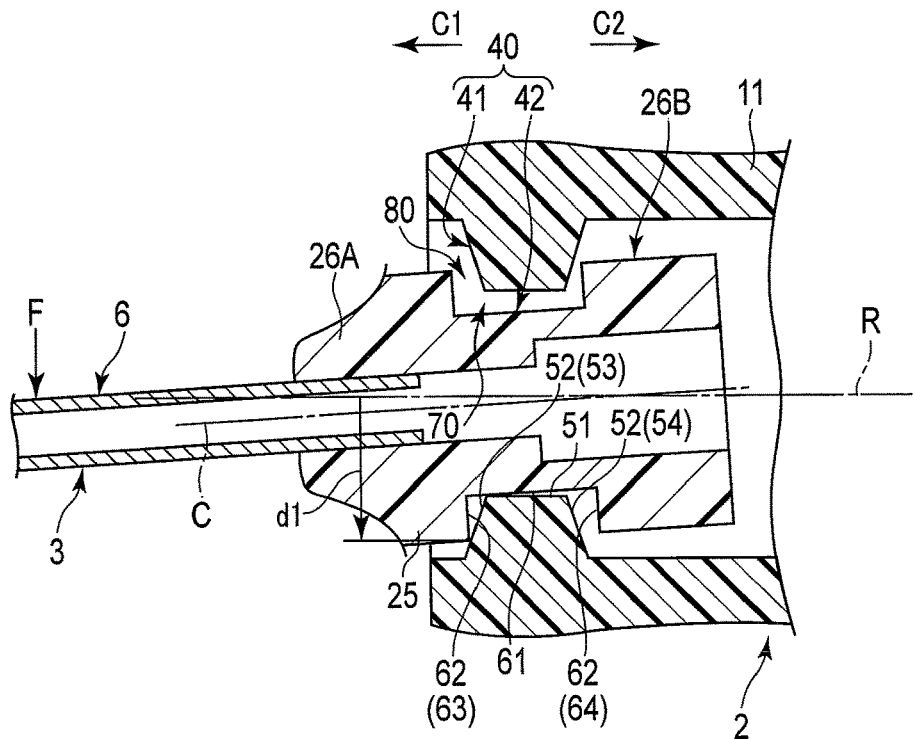
F I G. 5

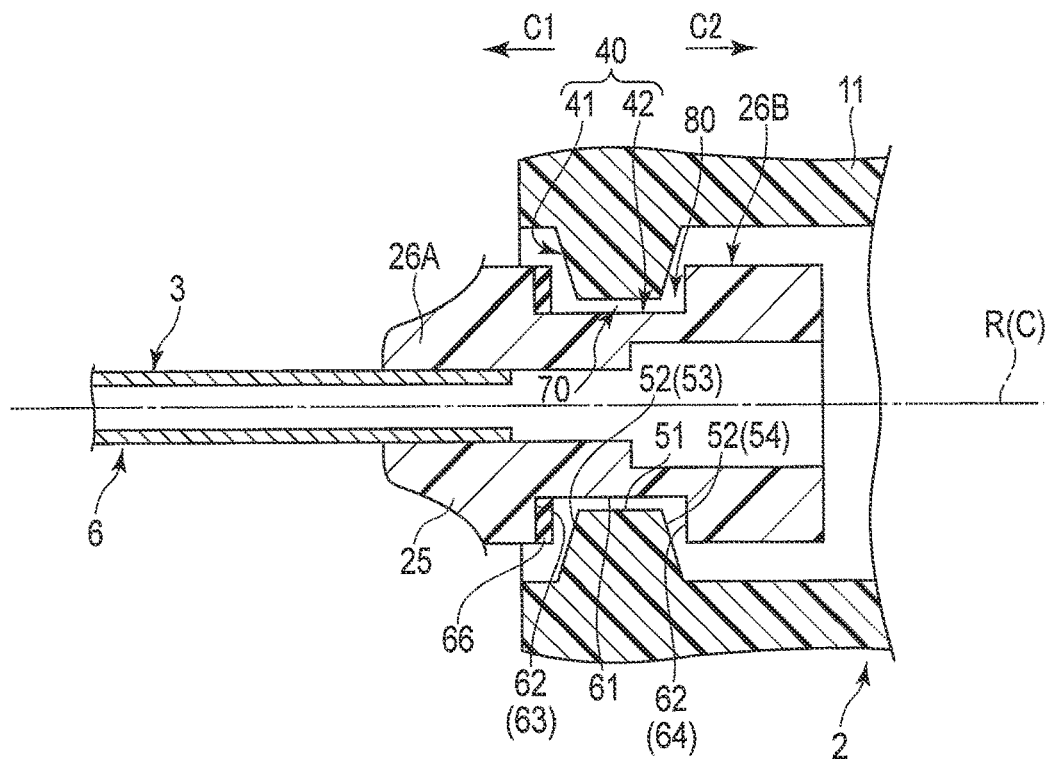
F I G. 10
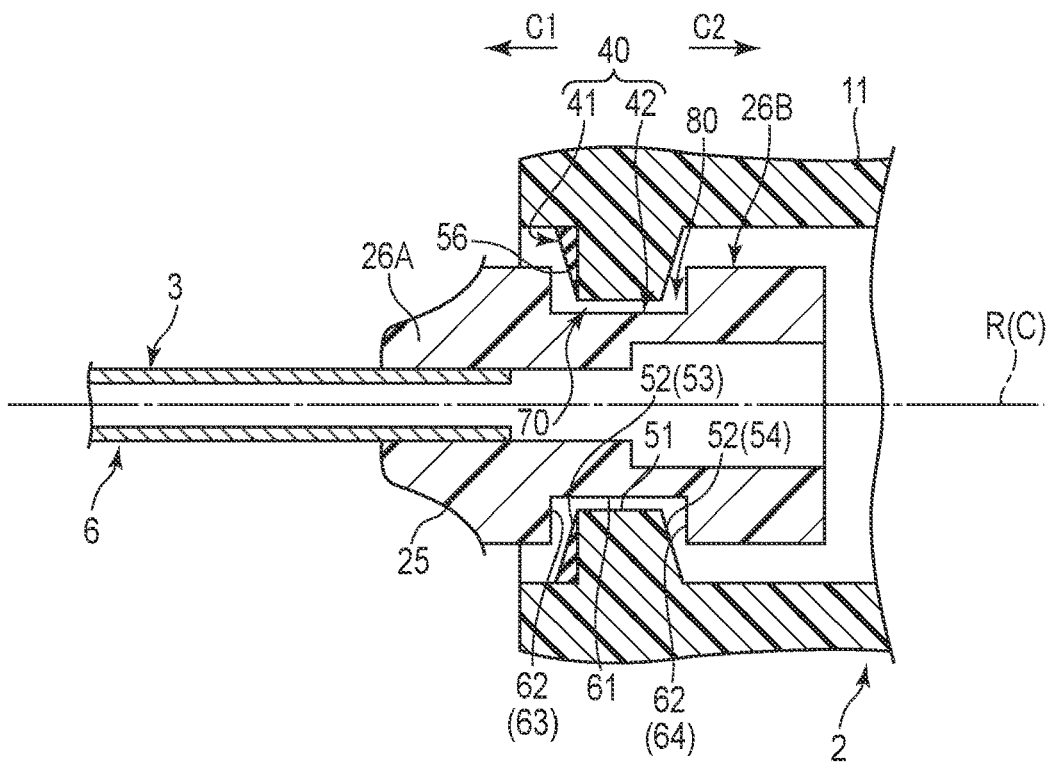
F I G. 11

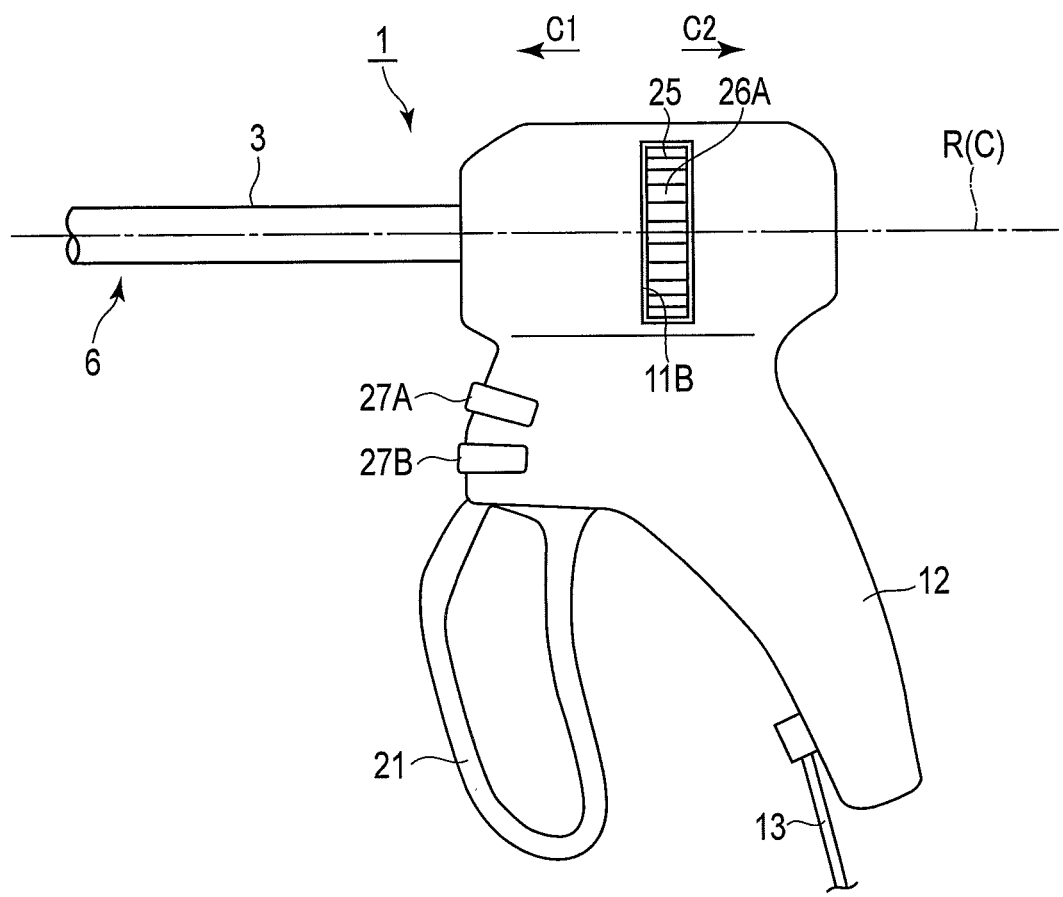
F I G. 15

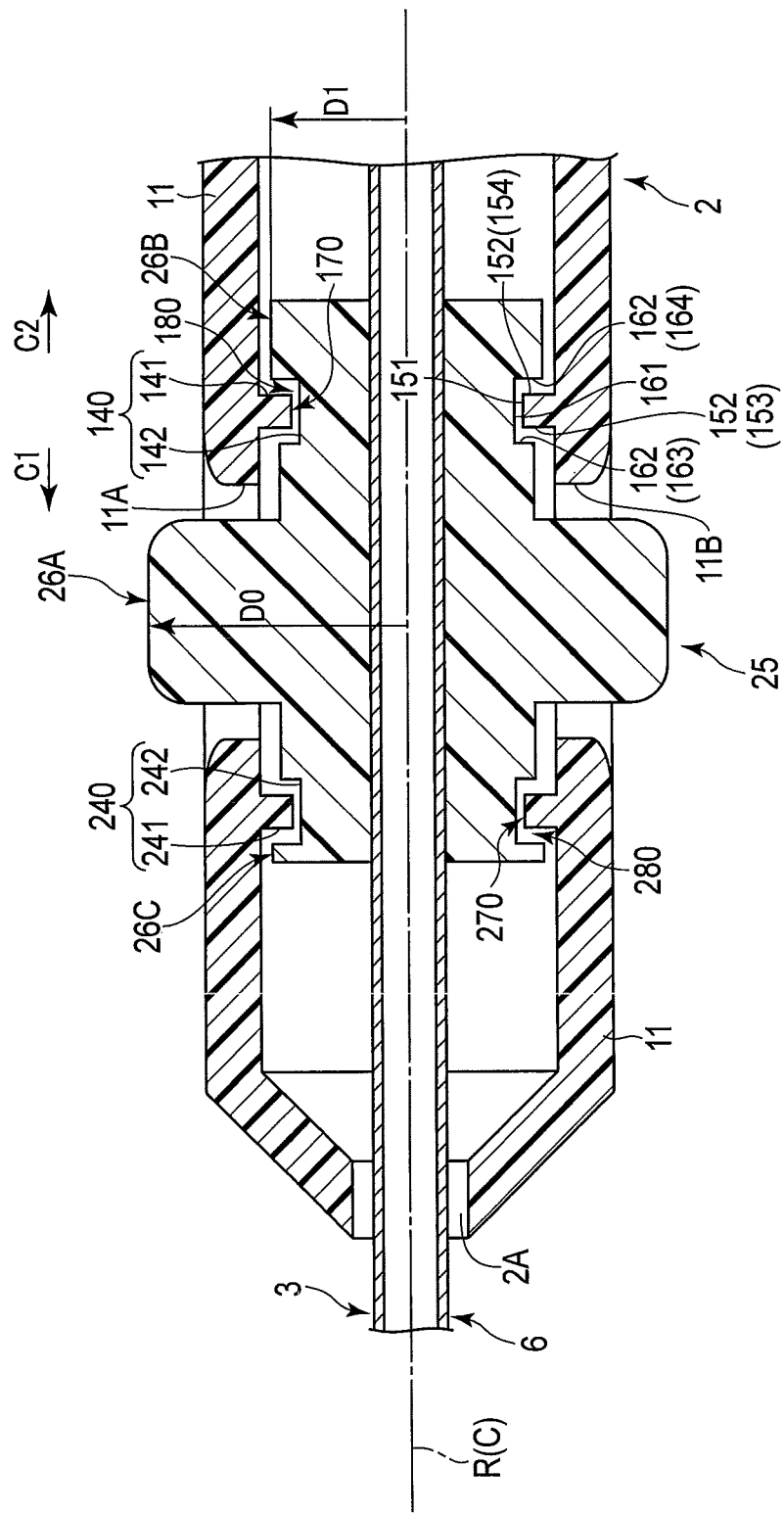
F I G. 16

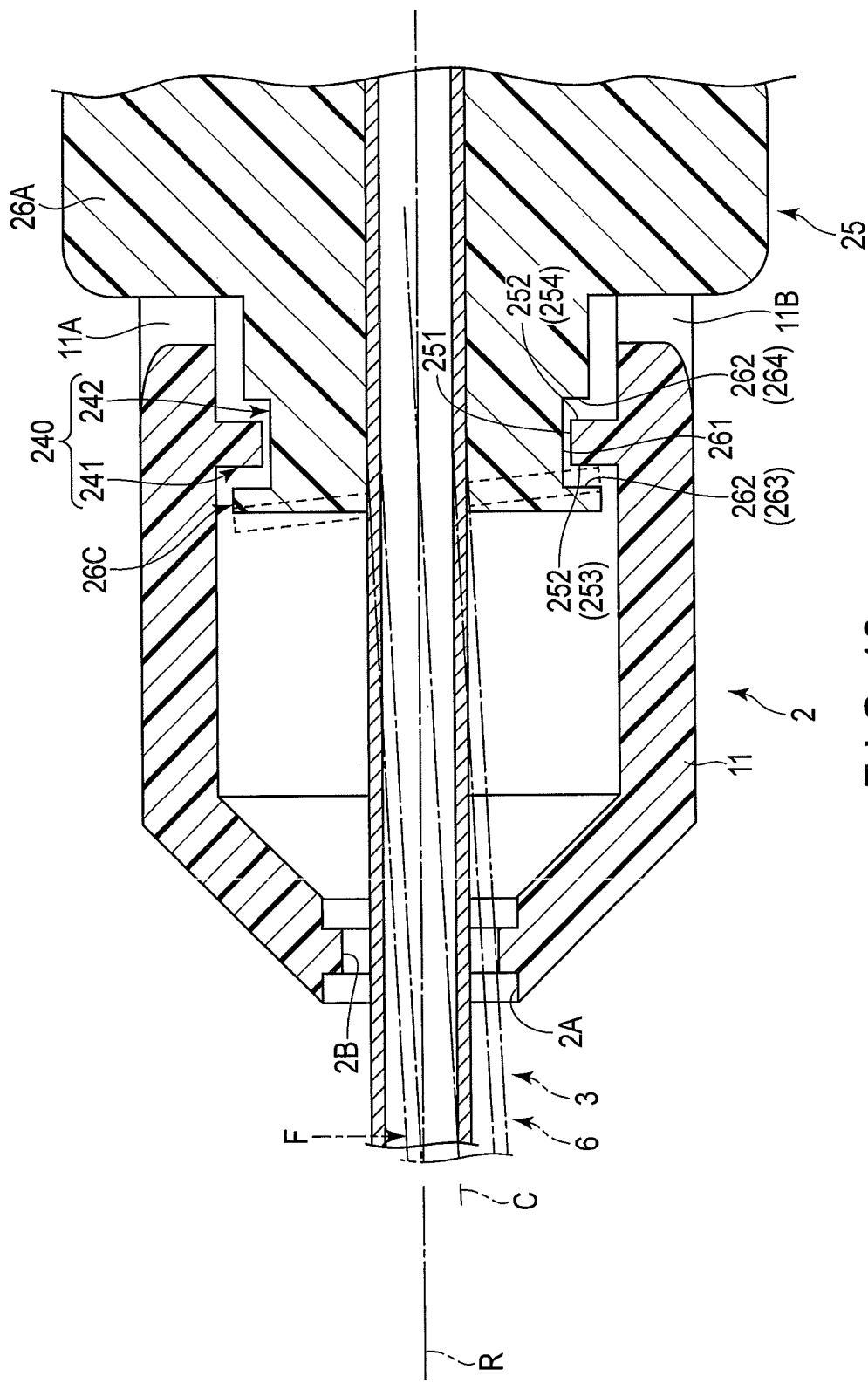
F I G. 18

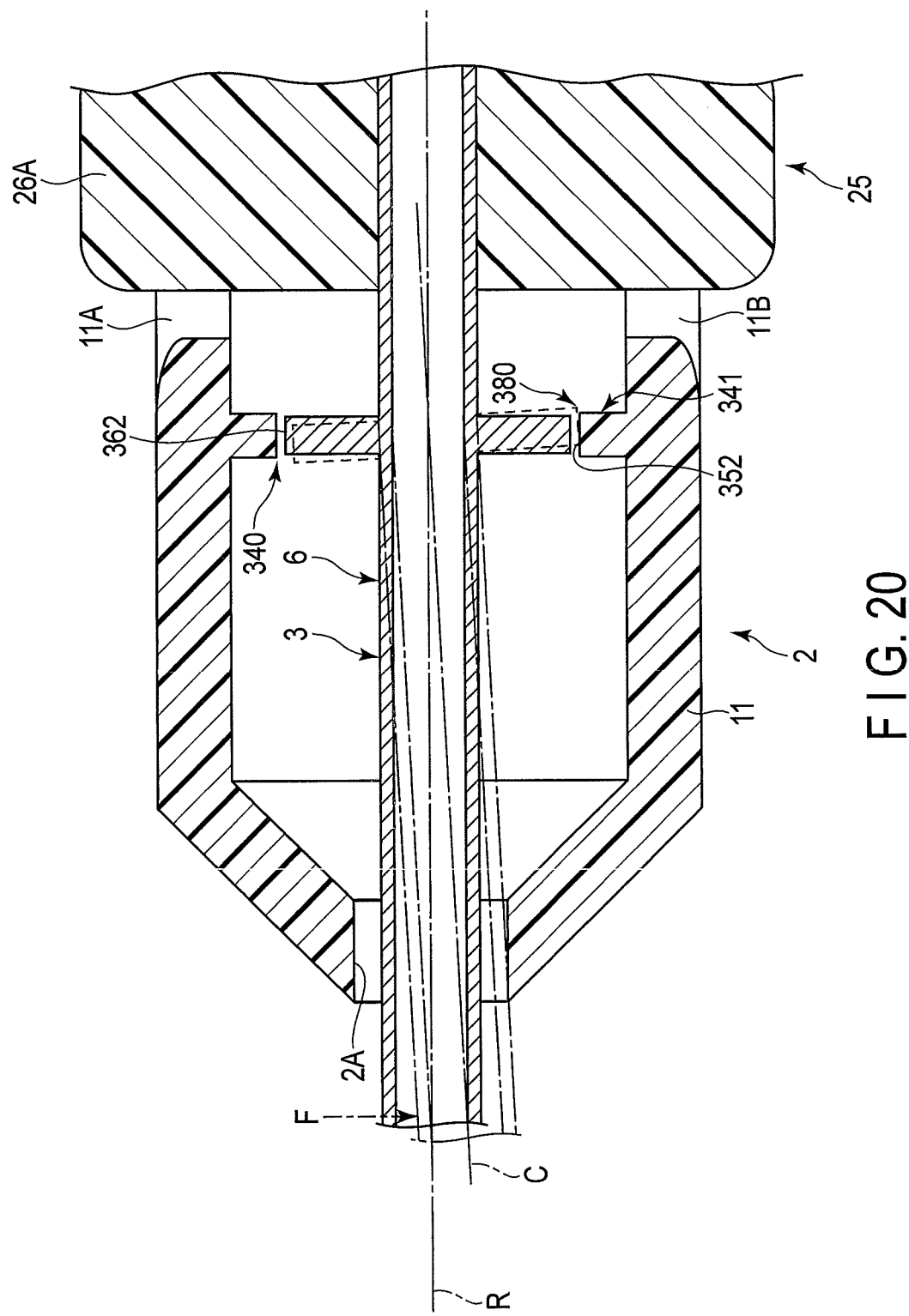
F I G. 20

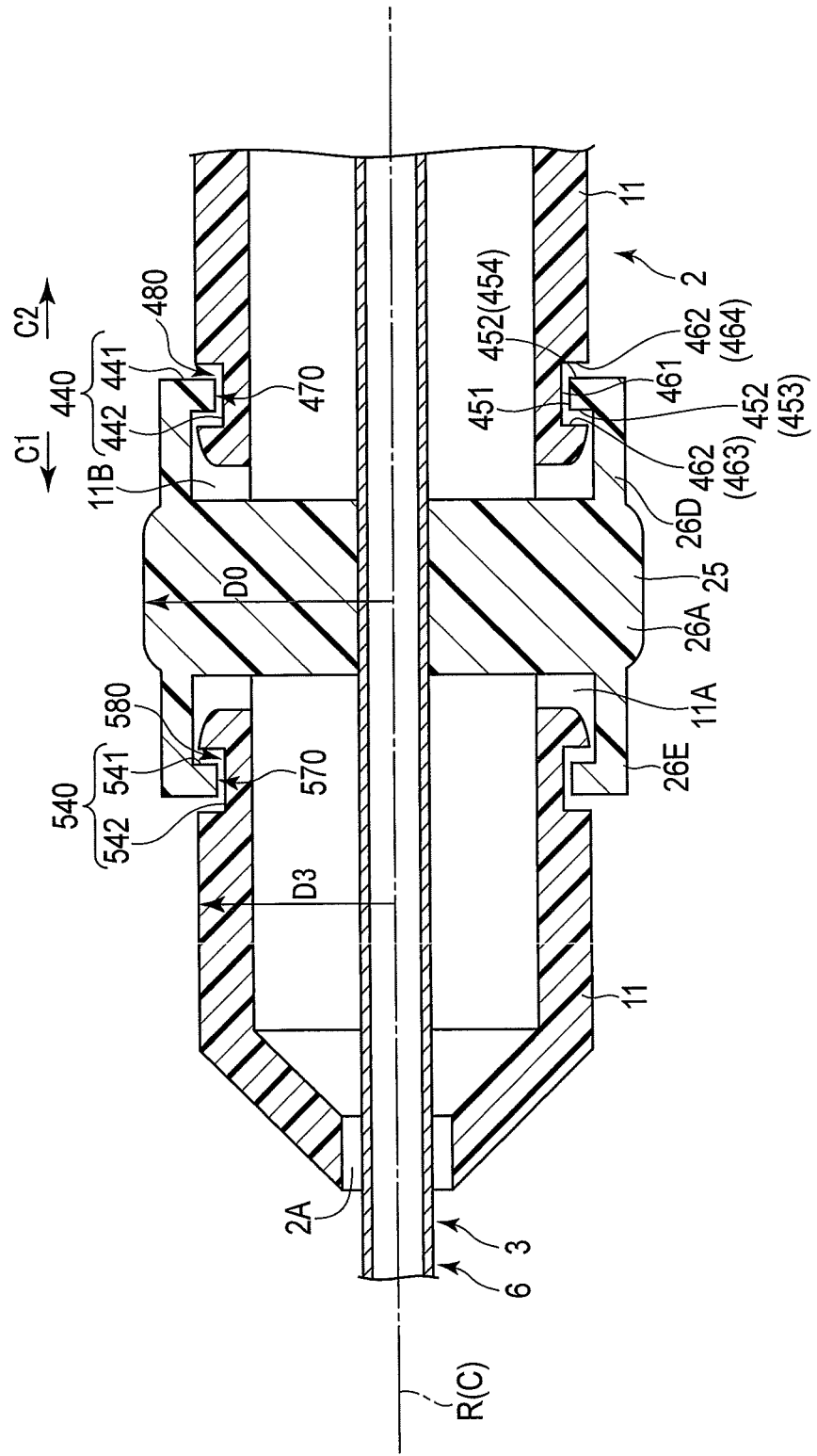
F I G. 21

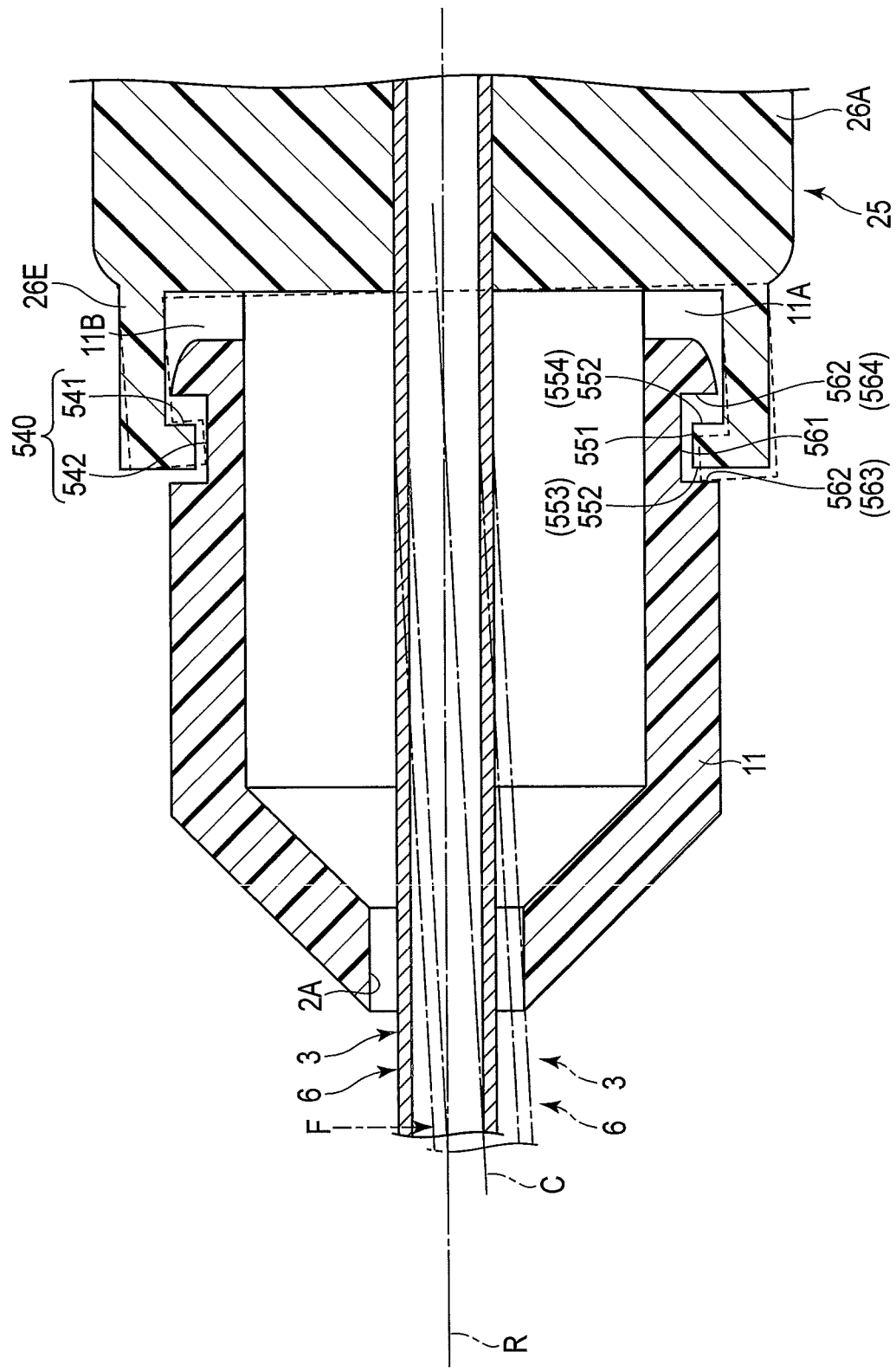
F I G. 22

TREATMENT INSTRUMENT

CROSS-REFERENCE TO RELATED APPLICATIONS

This application is a Continuation Application of PCT Application No. PCT/JP2016/068287, filed Jun. 20, 2016, the entire contents of all of which are incorporated herein by reference.

BACKGROUND OF THE INVENTION

1. Field of the Invention

The present invention generally relates to a treatment instrument that is configured to treat a treatment target with an end effector.

2. Description of the Related Art

U.S. Pat. No. 5,383,888 discloses a treatment instrument in which an end effector that treats a treatment target is provided at a distal end of a shaft. In this treatment instrument, a shaft is connected to a retainable housing, and by opening or closing a handle relative to a grip of the housing, a space between a pair of grasping pieces is opened or closed in the end effector. By the space between the grasping pieces being closed, a treatment target, such as a living tissue, is grasped between the grasping pieces. In addition, a rotating member (rotating knob) which is a part of the shaft is attached to the housing so as to be rotatable around a central axis of the shaft as a center. When an operating force that rotates the rotating member is applied, the shaft and the end effector rotate relative to the housing together with the rotating member with the central axis of the shaft as a predetermined rotation axis. As a result, an angular position of the end effector around the predetermined rotation axis changes. Furthermore, in this treatment instrument, the end effector bends with respect to the shaft (the central axis of the shaft) based on an operation with a bending operation portion (wing member) provided in the housing.

BRIEF SUMMARY OF THE INVENTION

According to one aspect of the present invention, a treatment instrument includes a rotating body and a housing. The rotating body includes a shaft which extends along a longitudinal axis; an end effector which is disposed on a distal side of the shaft; and a connecting portion including: a supported portion having a cylindrical outer peripheral surface, and an engaged portion which is adjacent to the supported surface. The housing includes a supporting portion which is configured to support the supported portion of the rotating body, the supporting portion being rotatable around a predetermined rotation axis; and an engaging portion that is configured to generate a frictional force larger than a frictional force between the supporting portion and the supported portion by coming into contact with the engaged portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a schematic cross-sectional diagram showing a state in which a central axis of a shaft coincides with a predetermined rotation axis of the housing in the treatment instrument according to the first embodiment.

FIG. 5 is a schematic cross-sectional diagram showing a state in which the central axis of the shaft is shifted with respect to the predetermined rotation axis of the housing when a rotary element receives an external force from a direction deviated from the central axis (predetermined rotation axis), in the treatment instrument according to the first embodiment.

FIG. 10 is a schematic cross-sectional diagram showing a state in which a friction plate for effectively generating a frictional force against the housing is arranged in the rotating member, in a treatment instrument according to a fourth modification of the first embodiment.

FIG. 11 is a schematic cross-sectional diagram showing a state in which a friction plate for effectively generating a frictional force against the rotating member is arranged in the housing, in a treatment instrument according to a fifth modification of the first embodiment.

FIG. 15 is a schematic diagram showing a treatment instrument according to a third embodiment with the end effector omitted from the drawing.

FIG. 16 is a schematic cross-sectional diagram showing a state in which a central axis of a shaft coincides with a predetermined rotation axis of a housing, in the treatment instrument according to the third embodiment.

FIG. 18 is a schematic cross-sectional diagram showing a state in which the central axis of the shaft coincides with the predetermined rotation axis of the housing by a solid line, and a state in which the central axis of the shaft is shifted with respect to the predetermined rotation axis of the housing when the rotary element receives an external force from a direction deviated from the central axis, and an outer peripheral surface of the shaft comes into contact with a friction ring at a distal end of the housing by a broken line, in a treatment instrument according to a first modification of the third embodiment.

FIG. 20 is a schematic cross-sectional diagram showing a state in which the central axis of the shaft coincides with the predetermined rotation axis of the housing by a solid line, and a state in which the central axis of the shaft is shifted with respect to the predetermined rotation axis of the housing when a rotary element receives an external force from a direction deviated from the central axis by a broken line, in the treatment instrument according to the second modification of the third embodiment.

FIG. 21 is a schematic cross-sectional diagram showing a state in which the central axis of the shaft coincides with the predetermined rotation axis of the housing, in a treatment instrument according to a fourth embodiment.

FIG. 22 is a schematic cross-sectional diagram showing a state in which the central axis of the shaft coincides with the predetermined rotation axis of the housing by a solid line, and a state in which the central axis of the shaft is shifted with respect to the predetermined rotational axis of the housing when the rotary element receives an external force from a direction deviated from the central axis by a broken line, in the treatment instrument according to the fourth embodiment.

DETAILED DESCRIPTION OF THE INVENTION

First Embodiment

Figure 1:
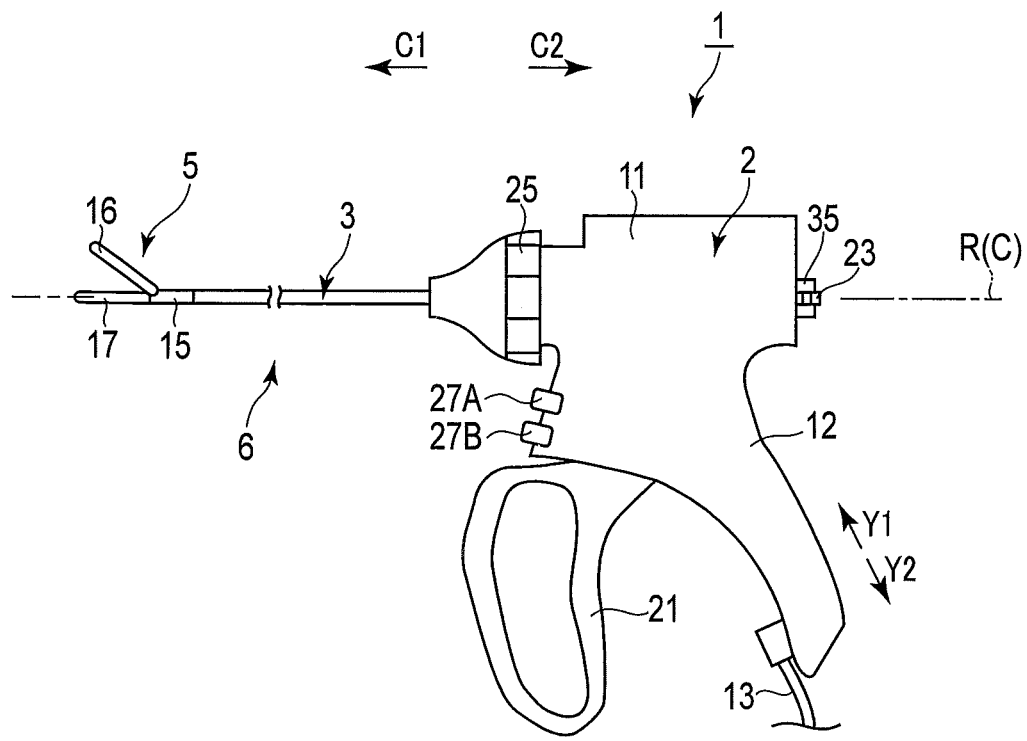
FIG. 1 is a schematic diagram showing a treatment instrument according to a first embodiment.

A first embodiment of the present invention will be described with reference to FIGS. 1 to 5. FIG. 1 is a diagram showing a treatment instrument (grasping treatment instrument) 1 of the present embodiment. The treatment instrument 1 shown in FIG. 1 includes a predetermined rotation axis (longitudinal axis) R. Herein, one side in a direction along the predetermined rotation axis R is defined as a distal end side (an arrow C1 side), and a side opposite to the distal end side is defined as a proximal end side (an arrow C2 side).

The treatment instrument 1 includes a housing 2, a shaft (sheath) 3 protruding with respect to the housing 2, and an end effector 5. The shaft 3 and the end effector 5 form a rotary element (rotating body) 6 with respect to the predetermined rotation axis R of the housing 2. That is, the rotary element 6 includes the shaft 3 and the end effector 5.

A central axis C is defined in the shaft 3. The shaft 3 extends from the proximal end side to the distal end side along the central axis C. The end effector 5 is disposed at the distal end of the shaft 3. The shaft 3 is rotatably supported with respect to the housing 2. Thus, the shaft 3 supports the end effector 5 together with the shaft 3 so as to be rotatable around the central axis C. A side of the shaft 3 toward the housing 2 is the proximal end side, and a side toward the end effector 5 is the distal end side. The end effector 5 may be arranged on the central axis C, or may be arranged at a position shifted from the central axis C. As will be described later, in the present embodiment, the end effector 5 can move between a position arranged on the central axis C of the shaft 3 and a position arranged at a position shifted from the central axis C. Thus, in the present embodiment, the end effector 5 is bent with respect to the shaft 3.

It is preferable that the shaft 3 is made of, for example, a metallic material such as a stainless steel material, and can be elastically deformed by a load of an external force F applied to the rotary element 6 from a direction deviated from the central axis C (the predetermined rotation axis R). For this reason, it is preferable that the shaft 3 has a bendability of bending appropriately by the load of the external force F applied to the rotary element 6 from a direction deviated from the central axis C (the predetermined rotation axis R).

The housing 2 is made of a resin material having electrical insulation properties. The housing 2 according to the present embodiment includes a housing main body 11 extending along a predetermined (immovable) rotation axis R, and a grip (fixed handle) 12 extending from the housing main body 11 along a direction (a direction indicated by arrows Y1 and Y2) intersecting the predetermined rotation axis R. The grip 12 is provided at a portion away from the predetermined rotation axis R. One end of a cable 13 is connected to the grip 12. The other end of the cable 13 is connected to an energy control device (not shown). It should be noted here that a direction intersecting (substantially vertical to) the predetermined rotation axis R and intersecting (substantially vertical to) the extending direction of the grip 12 is defined as a width direction (a direction substantially vertical to a paper surface in FIG. 1) of the housing 2. FIG. 1 is a diagram of the treatment instrument 1 as viewed from one side in the width direction of the housing 2.

Figure 2:
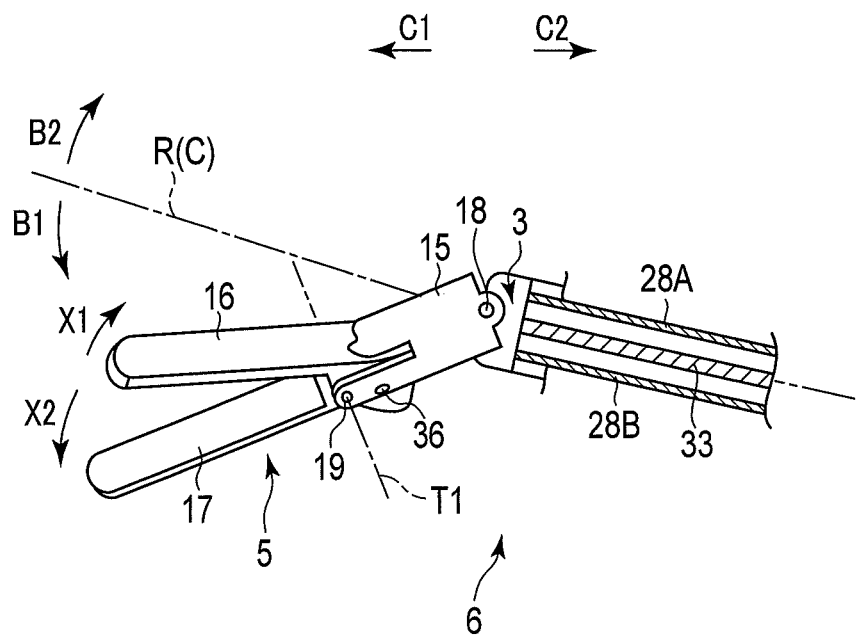
FIG. 2 is a schematic perspective diagram showing a configuration of an end effector in the treatment instrument according to the first embodiment.

FIG. 2 is a diagram showing a configuration of the end effector 5. As shown in FIGS. 1 and 2, the end effector 5 is rotatable relative to the housing 2 around the rotation axis R (central axis C) together with the shaft 3, and is bendable relative to the shaft 3 (central axis C). It is preferable that the end effector 5 is rotatable relative to the housing 2 around the rotation axis R (central axis C) together with the shaft 3, and is capable of bending relative to the shaft 3 (central axis C) (see FIG. 14B). As the shaft 3 rotates around the central axis C, an angular position around the rotation axis R of the end effector 5 changes. Furthermore, a bending direction (directions indicated by arrows B1 and B2) of the end effector 5 intersects (substantially vertical to) the predetermined rotation axis R. The end effector 5 includes a relay member 15, a first grasping piece 16, and a second grasping piece 17. The relay member 15 is attached to the distal end of the shaft 3 so as to be bendable relative to the shaft 3. That is, a bending joint 18 is formed between the shaft 3 and the relay member 15. In addition, in the end effector 5, the space between a pair of grasping pieces 16 and 17 can be opened and closed. Opening and closing directions (directions indicated by arrows X1 and X2) of the grasping pieces 16 and 17 intersect the central axis C, and intersect the inflecting direction of the end effector 5.

As shown in FIG. 2, the first grasping piece 16 is pivotably attached to the relay member 15 via a supporting pin (supporting portion) 19. That is, the relay member 15 is provided with the supporting pin 19 that supports the first grasping piece 16. The first grasping piece 16 is pivotable about the supporting pin 19 as a center. In the present embodiment, a pivot axis T1 of the first grasping piece 16 with respect to the relay member 15 passes through the supporting pin 19, and is substantially coaxial with a central axis of the supporting pin 19. Then, the pivot axis T1 extends substantially in parallel with the bending direction of the end effector 5. That is, an extension direction of the pivot axis T1 intersects the central axis C of the shaft 3, and intersects the opening and closing directions of the grasping pieces 16 and 17. As the first grasping piece 16 rotates about the supporting pin (supporting portion) 19 as a center, the first grasping piece 16 opens or closes relative to the second grasping piece 17. In addition, the supporting pin (supporting portion) 19, together with the shaft 3 and the end effector 5, is rotatable around the predetermined rotation axis R relative to the housing 2.

Herein, in one embodiment, the second grasping piece 17 is formed integrally with or fixed to the relay member 15. In another embodiment, the second grasping piece 17 is also pivotally attached to the relay member 15. Furthermore, in another embodiment, a rod member (not shown) extends from an internal portion of the relay member 15 toward the distal end side, and the second grasping piece 17 is formed by a protruding portion of the rod member from the relay member 15 to the distal end side.

As shown in FIG. 1, a handle (movable handle) 21 is turnably attached to the housing 2. As the handle 21, which is an opening/closing operation input portion, turns relative to the housing 2, the handle 21 opens or closes relative to the grip 12. That is, the handle 21 can be opened and closed relative to the grip 12. In the present embodiment, since it is the pistol type treatment instrument 1, the handle 21 is positioned on a side where the grip 12 is positioned with respect to the rotation axis R and on the distal end side with respect to the grip 12. A movement direction of the handle 21 in the opening operation and the closing operation relative to the grip 12 is substantially parallel to the rotation axis R. In some embodiments, the handle 21 may be provided on the proximal end side with respect to the grip 12. In another embodiment, the handle 21 and the grip 12 are provided on opposite sides to each other with the rotation axis R as a center, and a moving direction of the handle 21 in the opening operation and the closing operation relative to the grip 12 may be substantially vertical to the rotation axis R.

In addition, in the present embodiment, a rotating dial (operation element) 23 is attached to the housing 2 as a bending operation input unit (operation input unit). For example, by turning the rotating dial 23, an operation of bending the end effector 5 relative to the shaft 3 is inputted. As shown in FIG. 2, bending drive members 28A and 28B, such as wires or leaf springs, extend along the rotation axis R in an internal portion of the shaft 3. Distal ends (one ends) of the bending drive members 28A and 28B are connected to the relay member 15 of the end effector 5. In addition, proximal ends of the bending drive members 28A and 28B are mechanically connected to the rotating dial 23 via a pulley (not shown), etc. provided in an internal portion of the housing 2. Operation input is performed by the rotating dial (bending operation input unit) 23, whereby an operating force is transmitted to the bending drive members 28A and 28B, and the bending drive members 28A and 28B move along the predetermined rotation axis R (central axis C) relative to the shaft 3 and the housing 2. Thereby, the end effector 5 is bent relative to the shaft 3 (central axis C) in the bending direction (the directions indicated by the arrows B1 and B2).

Herein, the bending drive members 28A and 28B are rotatable relative to the housing 2 around the predetermined rotation axis R (central axis C) together with the shaft 3 and the end effector 5. In addition, the rotating dial 23 may be rotatable around the predetermined rotation axis R (central axis C) relative to the housing 2 together with the shaft 3 and the end effector 5, and may not rotate together with the shaft 3 and the end effector 5 around the predetermined rotation axis R (central axis C). Furthermore, in the present embodiment, the rotating dial 23 is attached to a proximal end surface of the housing main body 11, but a position of the rotating dial 23 is not limited thereto. For example, a bending operation input unit, such as the rotating dial 23, may be attached to an outer surface of the housing main body 11 facing a side opposite to a side on which the grip 12 is positioned with respect to the predetermined rotation axis R.

A rotating member 25, which is a part of the shaft 3, is supported on the distal end side of the housing main body 11. It is preferable that the rotating member 25 is formed of a resin material having electrical insulation properties. The rotating member 25 includes a rotating knob 26A to be operated and a connecting portion 26B to be connected to the housing 2. The rotating knob 26A and the connecting portion 26B are formed in an appropriate cylindrical shape. In order to generate a large rotational moment with a small force, the maximum radius (distance from the central axis C) D0 of the rotating knob 26A is appropriately large. It is preferable that the maximum radius (distance from the central axis C) D0 of the rotating knob 26A is formed larger than the maximum radius (distance from the central axis C) D1 of the connecting portion 26B.

The shaft 3 is supported by the housing 2 in a state of being inserted into an internal portion of the housing main body 11 from the distal end side. The rotating member 25 is fixed to the shaft 3, and rotates together with the shaft 3 and the end effector 5 around the rotation axis R relative to the housing 2.

In the present embodiment, an operating force for rotating the shaft 3 and the end effector 5, that is, the rotary element 6 around the predetermined rotation axis R (central axis C) is applied to the rotating member 25 as the rotating operation input unit.

Operation buttons 27A and 27B are attached to the housing 2. Each of the operation buttons 27A and 27B is pressed to perform operation input. When an operation input is made by each of the operation buttons 27A and 27B, the treatment instrument 1 is operated in a predetermined operation mode. At this time, for example, similarly to known treatment instruments, either high-frequency current, ultrasonic vibration, or heater heat is applied as a treatment energy to the treatment target grasped between the grasping pieces 16 and 17. In one embodiment, when the treatment instrument 1 is operated in a predetermined operation mode on the basis of an operation input of any one of the operation buttons 27A and 27B, an electric motor is driven so that a staple may be pierced into the treatment target grasped between the grasping pieces 16 and 17.

Figure 3:
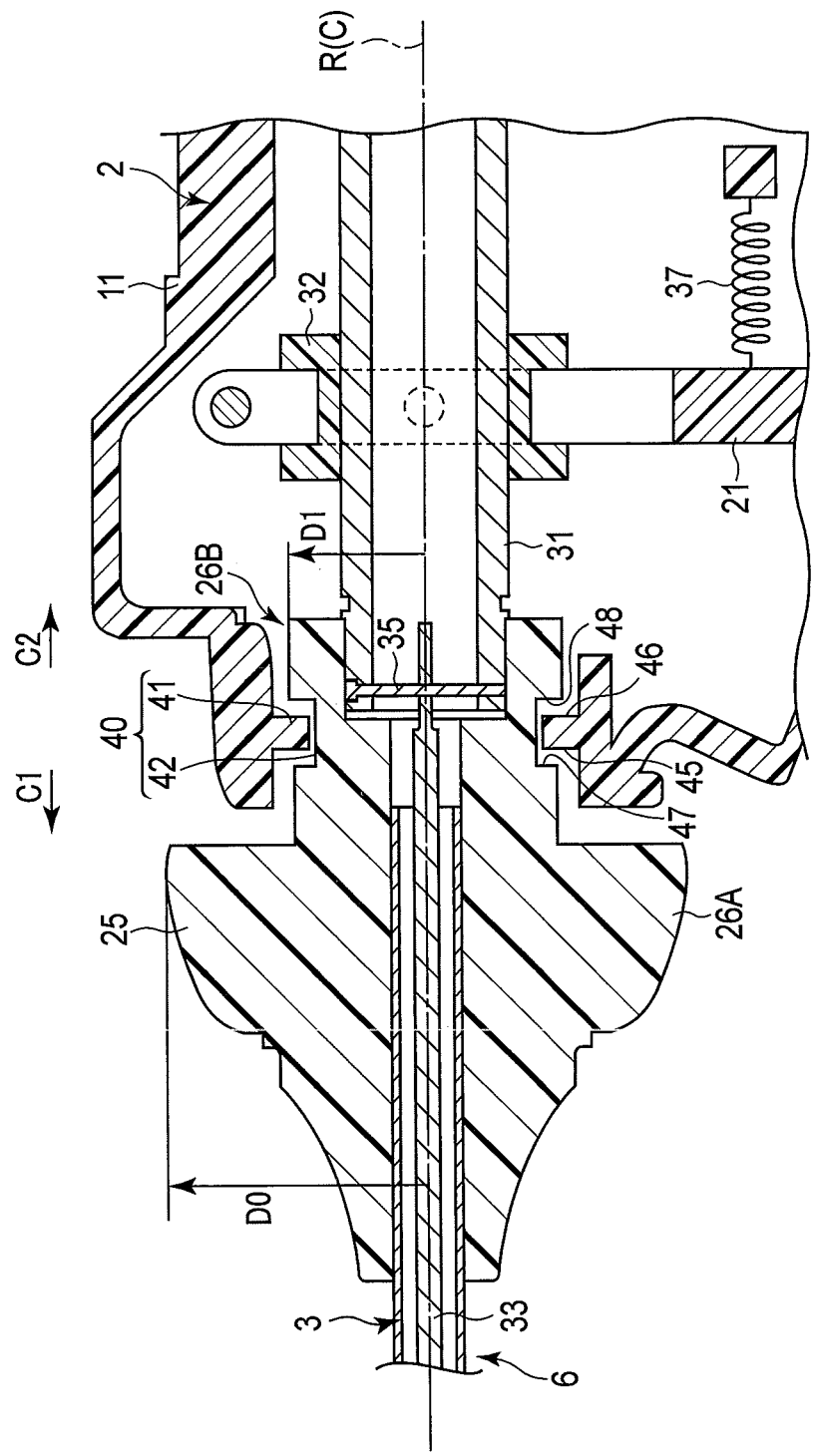
FIG. 3 is a schematic cross-sectional diagram showing an inner configuration of a housing in the treatment instrument according to the first embodiment.

FIG. 3 is a diagram showing a configuration of the internal portion of the housing 2. FIG. 3 shows a cross section that is substantially vertical to (intersecting) the width direction of the housing 2. In addition, in FIG. 3, the bending drive members 28A and 28B, and a configuration for transmitting the operating force from the rotating dial 23 to the inflection drive members 28A and 28B, etc. are omitted. As shown in FIG. 3, in the internal portion of the housing (housing main body 11), a tubular movable member 31 is attached to the rotating member 25 from the proximal end side (arrow C2 side). The movable member 31 extends along the predetermined rotation axis R (central axis C) and is movable along the predetermined rotation axis R relative to the housing 2 and the shaft 3. However, a rotation of the movable member 31 around the rotation axis R relative to the shaft 3 is restricted, and the movable member 31, together with the shaft 3 and the end effector 5, is rotatable around the predetermined rotation axis R relative to the housing 2.

As a mechanism that the first grasping piece 16 relatively performs an opening operation relative to the second grasping piece 17 by opening the handle 21 relative to the grip 12, and the first grasping piece 16 relatively performs a closing operation relative to the second grasping piece 17 by closing the handle 21 relative to the grip 12, various mechanisms can be adopted.

In the internal portion of the housing 2 according to the present embodiment, a slider member 32 is arranged on an outer peripheral surface of the movable member 31. The handle 21 is connected to the movable member 31 via the slider member 32. The movable member 31 is rotatable around the predetermined rotation axis R relative to the handle 21. In addition, in the internal portion of the housing 2, a driving rod 33, which is an opening/closing driving member, is fixed to the movable member 31 via a connecting pin 35. The driving rod 33 extends along the rotation axis R from the internal portion of the movable member 31 through the internal portion of the shaft 3. Since the driving rod 33 is fixed to the movable member 31, when the operating force of the rotating member 25 is applied, the driving rod 33 rotates together with the shaft 3, the end effector 5, and the movable member 31 around the predetermined rotation axis R (central axis C) relative to the housing 2.

An urging member 37, such as a spring, is provided in the internal portion of the housing 2. One end of the urging member 37 is connected to the housing 2, and the other end is connected to the handle 21. The urging member 37 urges the handle 21 to be in a state of opening relative to the grip 12.

By applying an operating force to the handle 21 and opening or closing the handle 21 relative to the grip 12, the movable member 31 and the driving rod 33 move along the predetermined rotation axis R (central axis C) relative to the shaft 3 and the housing 2. As shown in FIG. 2, one end (distal end) of the driving rod (driving member) 33 extending through the internal portion of the shaft 3 is connected to the first grasping piece 16 of the end effector 5. In the present embodiment, the driving rod 33 is connected to the first grasping piece 16 via a connection pin 36. As the movable member 31 and the driving rod (driving member) 33 move along the predetermined rotation axis R, at least the first grasping piece 16 turns about a support pin 19 with respect to the relay member 15. As a result, the space between the grasping pieces 16 and 17 is opened or closed. At this time, the support pin 19 serves as a fulcrum for pivotal movement of the first grasping piece 16, and the connection pin 36 serves as a force point for exerting a driving force from the driving rod 33 to the first grasping piece 16. In an embodiment in which the second grasping piece 17 is also rotatable relative to the relay member 15, a distal end of the driving rod (opening and closing driving member) 33 is connected to the second grasping piece 17 in addition to the first grasping piece 16. In this case, as the driving rod 33 moves along the rotation axis R, both of the grasping pieces 16 and 17 turn relative to the relay member 15, and the space between the grasping pieces 16 and 17 is opened or closed.

In the present embodiment, by the urging member 37, the first grasping piece 16 is urged to a state of being opened with respect to the second grasping piece 17, and the end effector 5 is urged to a state in which the space between the grasping pieces 16 and 17 is opened.

As shown in FIGS. 3 and 4, the housing main body 11 of the housing 2 is provided with an engagement projection (supporting portion) 41 protruding toward the predetermined rotation axis R. Thus, in the present embodiment, the engagement projection 41 is arranged on an inner peripheral surface of the housing 2. As an example, the engagement projection (inner flange) 41 is provided over the entire circumference around the predetermined rotation axis R. Although not shown, the engagement projection 41 may be formed, for example, at appropriate intervals in a circumferential direction around the predetermined rotation axis R. Thus, one engagement projection 41 may be provided, or a plurality of engagement projections 41 may be provided.

An engagement recess (supported portion) 42 that is recessed toward the inner peripheral side is provided in the connecting portion 26B of the rotating member 25 which is a part of the shaft 3. The engagement recess 42 is provided over the entire circumference around the rotation axis R. By engaging the engagement projection 41 with the engagement recess 42, the shaft 3 is supported by the housing 2 so as to be rotatable around the predetermined rotation axis R.

Thus, the engagement recess 42 can move around the rotation axis R relative to the engagement projection 41. The rotating member 25 of the shaft 3 is rotatable around the predetermined rotation axis R relative to the housing 2. Accordingly, the engagement projection 41 and the engagement recess 42 form a joint assembly (connecting portion) 40 that connects the shaft 3 so as to be rotatable around the predetermined rotation axis R of the housing 2.

FIGS. 4 and 5 are diagrams showing a configuration of the joint assembly 40 (the engagement projection 41 and the engagement recess 42) between the shaft 3 and the housing 2. FIG. 4 shows a state in which the central axis C of the shaft 3 coincides with the predetermined rotation axis R of the housing 2. FIG. 5 shows a state in which the central axis C of the shaft 3 is shifted with respect to the predetermined rotation axis R of the housing 2 by an external force F to the rotary element 6, that is, the end effector 5 and/or the shaft 3.

As shown in FIGS. 4 and 5, the engagement projection 41 of the housing 2 includes a supporting portion (rotation supporting surface) 51 and an engaging portion (sliding resistance generating portion) 52. The supporting portion 51 defines a cylindrical inner peripheral surface with respect to the predetermined rotation axis R. The supporting portion 51 supports the rotary element 6 so as to be rotatable around the predetermined rotation axis R. The engaging portion 52 is adjacent to the supporting portion 51 along the central axis C. The engaging portion 52 includes a projection facing surface (first receiving surface) 53 facing the distal end side and a projection facing surface (second receiving surface) 54 facing the proximal end side.

The engagement recess 42 of the rotating member 25 of a part of the shaft 3 includes a supported portion (rotation supporting surface) 61 and an engaged portion (sliding resistance generating portion) 62. That is, the rotary element 6 includes the supported portion 61 provided on the shaft 3 and supported by the supporting portion 51 of the housing 2. The supported portion 61 defines a cylindrical outer peripheral surface with respect to the central axis C. The engaged portion 62 is adjacent to the supported surface 61 along the central axis C. The engaged portion 62 includes a recessed facing surface (first contact surface) 63 facing the proximal end side and a recessed facing surface (second contact surface) 64 facing the distal end side.

It is preferable that the supporting portion 51 and the supported portion 61 are formed of a material that suppresses generation of a frictional force when in contact, or are subjected to surface processing that suppresses generation of a frictional force. It is preferable that the supporting portion 51 and the supported portion 61 are formed of a material having a small friction coefficient, e.g. polyoxymethylene:POM, etc., and having good slidability (lubricity). Thus, the supported portion 61 can rotate smoothly relative to the supporting portion 51. In this way, in the present embodiment, the supporting portion 51 of the housing 2 and the supported portion 61 of the shaft 3 cooperate to form a rotation supporting mechanism 70.

The recessed facing surface (first contact surface) 63 facing the proximal end side of the engagement recess 42 faces the projection facing surface (first receiving surface) 53 facing the distal end side of the engagement projection 41. The recessed facing surface (second contact surface) 64 facing the distal end side of the engagement recess 42 faces the projection facing surface (second receiving surface) 54 facing the proximal end side of the engagement projection 41. The projection facing surface 53 of the engagement projection 41 and the recessed facing surface 63 of the engagement recess 42, and the projection facing surface 54 of the engagement projection 41 and the recessed facing surface 64 of the engagement recess 42, each, are formed so as to generate a large frictional force when in contact, as compared with the frictional force (sliding resistance) between the supporting portion 51 and the supported portion 61. For example, the projection facing surface 53 of the engagement projection 41 and the recessed facing surface 63 of the engagement recess 42 are preferably formed of a material that generates a large frictional force when in contact, or are subjected to surface processing so as to easily generate a frictional force. Similarly, the projection facing surface 54 of the engagement projection 41 and the recessed facing surface 64 of the engagement recess 42 are preferably formed of a material that generates a large frictional force when in contact, or are subjected to surface processing so as to easily generate a frictional force.

In the present embodiment, the engaging portion 52 of the housing 2 and the engaged portion 62 of the shaft 3 cooperate to form a lock mechanism 80. In the present embodiment, the lock mechanism 80 is disposed in the supporting portion 51 of the housing 2 and the supported portion 61 of the shaft 3. Then, the lock mechanism 80 suppresses the rotation of the rotary element 6 around the predetermined rotation axis R, as one of positions of the rotary element 6 closer to the end effector 5 than a support position supported by the supporting portion 51 deviates from the predetermined rotation axis R. Herein, the rotation of the rotary element 6 around the predetermined rotation axis R is suppressed at a (different) position (the projection facing surface 53 of the engaging portion 52) adjacent to the supporting portion 51. Specifically, the engaging portion (frictional resistance portion) 52 cooperates with the engaged portion 62, and generates a sliding resistance in a direction around the axis of the predetermined rotation axis R at a position more apart from the predetermined rotation axis R than the supporting portion 51.

As shown in FIG. 4, the engaging portion 52 of the housing 2 is located adjacent to the distal end side and the proximal end side of the supporting portion 51 along the predetermined rotation axis R. Thus, the position of the supporting portion 51 of the housing 2 and the position of the engaging portion 52 are different from each other. Similarly, the engaged portion 62 of the shaft 3 is located adjacent to the distal end side and the proximal end side of the supported portion 61 along the central axis C. Thus, the position of the supported portion 61 of the shaft 3 and the position of the engaged portion 62 are different from each other.

In the rotation supporting mechanism 70, the supporting portion 51 of the engagement projection 41 of the housing 2 and the supported portion 61 of the engagement recess 42 of the shaft 3 cooperate with each other, to make the central axis C of the shaft 3 coincide with the predetermined rotation axis R of the housing main body 11 of the housing 2. Herein, an inner diameter of the supporting portion 51 with respect to the rotation axis R is larger than an outer diameter of the supported portion 61 with respect to the central axis C. At this time, the supporting portion 51 of the engagement projection 41 of the housing 2 is rattled, that is, plays with respect to the supported portion 61 of the engagement recess 42 of the shaft 3. In this state, when an operator rotates the rotating knob 26A of the rotating member 25, the central axis C of the shaft 3 rotates in a state coincident with or parallel to the predetermined rotation axis R of the housing 2.

In the position shown in FIG. 4, an outer peripheral surface of the supported portion 61 of the rotating member 25 and an inner peripheral surface of the supporting portion 51 of the housing 2 can partially contact each other. At this time, depending on a relationship between the outer diameter of the supported portion 61 of the rotating member 25 and the inner diameter of the supporting portion 51 of the housing 2, the supported portion 61 of the rotating member 25 moves (escapes) to an opposite side across the predetermined rotation axis R relative to the position (a state in which the central axis C is parallel to the predetermined rotation axis R) of the supporting portion 51 of the housing 2 which is currently in contact, and can make the central axis C of the shaft 3 coincide with or close to the predetermined rotation axis R of the housing 2. Thus, when the rotating member 25 is rotated about the axis of the predetermined rotation axis R (central axis C) relative to the housing 2, the rotating member 25 can be rotated in a state in which the sliding resistance is reduced (minimized). Therefore, in a state in which the predetermined rotation axis R of the housing 2 and the central axis C of the shaft 3 are made to coincide with each other, the joint assembly 40 minimizes the sliding resistance around the predetermined rotation axis R between the housing 2 and the shaft 3.

As shown in FIG. 5, at a position closer to the distal end of the end effector 5 than the rotating member 25 of the rotary element 6, that is, the end effector 5 and/or the shaft 3, a load (external force) F from a direction deviated from the rotation axis R of the housing 2 can be applied.

Particularly, in the present embodiment, the urging member 37 disposed in the internal portion of the housing 2 urges to a state where the first grasping piece 16 is opened relative to the second grasping piece 17. Thus, for example, even when the end effector 5 is on the axis of the central axis C of the shaft 3, when the external force F is applied from a side of the grasping piece 16 in a state where the first grasping piece 16 is opened with respect to the second grasping piece 17, a force to turn the end effector 5 about the central axis C is applied.

When the end effector 5 is at a position deviated from the central axis C of the shaft 3 and the external force F is applied to the end effector 5, a force to turn the end effector 5 about the central axis C is applied. This state can be maintained regardless of whether the first grasping piece 16 of the end effector 5 is opened or closed with respect to the second grasping piece 17.

It is to be noted that an unintended external force F around the central axis C may also be applied to the shaft 3 itself.

For this reason, a rotational moment around the central axis C may be generated on the end effector 5 and/or the shaft 3 by the external force F from a position deviated from the central axis C. The rotating member 25 which is a part of the shaft 3 tries to rotate around the central axis C. Herein, as described above, the supporting portion 51 of the engagement projection 41 of the housing 2 is rattled, that is, plays with respect to the supported portion 61 of the engagement recess 42 of the shaft 3. Thus, due to the load of the external force F on the end effector 5 and/or the shaft 3, the rotating member 25 is also inclined relative to the housing 2 due to rattling (play) with respect to the housing 2. That is, for example, as shown in FIG. 5, when an external force from a position deviated from the central axis C of the shaft 3 is applied to the rotary element 6, the central axis C of the shaft 3 is shifted from the predetermined rotational axis R of the housing 2, from a position shown in FIG. 4 to a position shown in FIG. 5. Thus, the central axis C of the shaft 3 is shifted with respect to the predetermined rotation axis R of the housing 2. At this time, the central axis C of the shaft 3 intersects or is arranged to be a skew positional relation with respect to the predetermined rotation axis R of the housing 2.

An example shown in FIG. 5 is intended to explain the present embodiment in an easily understandable manner. A maximum inclination angle (inclination amount) of the central axis C of the rotating member 25 (shaft 3) with respect to the predetermined rotation axis R of the housing 2 can be set as appropriate.

In the position shown in FIG. 5, the recessed facing surface 63 of the engaged portion 62 of the rotating member 25 is in contact with the projection facing surface 53 of the engaging portion 52 of the housing 2. At this time, a contact position (friction occurring position) between the projection facing surface 53 of the engaging portion 52 and the recessed facing surface 63 of the engaged portion 62 is at a position of a distance d1 (≥D1) in a radial direction with respect to the predetermined rotation axis R.

While the external force F is applied to the rotary element 6, the recessed facing surface 63 of the engaged portion 62 of the rotating member 25 continues to contact the projection facing surface 53 of the engaging portion 52 of the housing 2. Thus, a sliding resistance around the predetermined rotation axis R continues to be generated between the housing 2 and the rotating member 25. Accordingly, even if the external force F is applied to the rotary element 6 as shown in FIG. 5, and a force for rotating the end effector 5 and/or the shaft 3 around the central axis C is applied, a braking action due to a sliding resistance which suppresses the rotation around the predetermined rotation axis R relative to the housing 2 continues to be generated in the rotating member 25. As the external force F increases, an inclination amount with which the central axis C of the shaft 3 is inclined with respect to the predetermined rotation axis R of the housing 2 increases. As the inclination amount increases, the recessed facing surface 63 of the engaged portion 62 of the rotating member 25 gradually and strongly comes into contact with the projection facing surface 53 of the engaging portion 52 of the housing 2. Thus, as the external force F increases, the braking action due to the sliding resistance which suppresses the rotation of the shaft 3 (the rotating member 25) around the predetermined rotation axis R relative to the housing 2 also increases. Therefore, an unintentional rotation of the rotating member 25 relative to the housing 2 is suppressed. In this way, as the unintentional rotation of the rotating member 25 relative to the housing 2 is suppressed, the rotation around the central axis C of the shaft 3 is suppressed, and furthermore, the rotation of the end effector 5 around the central axis C is suppressed.

It is possible to rotate the rotating member 25 around the central axis C by an intention of the operator in a state where the external force F is applied to the end effector 5 and/or the shaft 3. In this case, the rotating member 25 may be rotated around the predetermined rotation axis R against the sliding resistance (frictional force) generated by the external force F between the rotating member 25 and the housing 2. As shown in FIG. 3, in the rotating member 25, there is an outer peripheral surface of the rotating knob 26A that places the operator's finger at a position (radius D0>D1), in particular, radially apart from the central axis C (predetermined rotation axis R). Thus, when the operator rotates the rotating member 25 around the central axis C, for reasons of moments based on a difference in size of radii D0 and D1, the rotating member 25 can be rotated against the sliding resistance (frictional force) generated between the rotating member 25 and the housing 2 with a smaller force. Therefore, for example, by turning the end effector 5 at a position shifted from the axis of the central axis C around the central axis C, the operator can push aside a biological tissue, for example, by the end effector 5. When the operator rotates the rotating member 25 against the frictional force (sliding resistance), the central axis C of the shaft 3 tries to move so as to coincide with the predetermined rotation axis R of the housing 2 so as to avoid friction between the engaging portion 52 and the engaged portion 62.

As described above, according to the treatment instrument 1 of the present embodiment, the following can be said.

In the treatment instrument 1 according to this embodiment, for example, by an external force F from a direction deviated from the predetermined rotation axis R, any one of the positions of the rotary element 6 which are closer to the end effector 5 than the support position supported by the supporting portion 51, can be shifted from the predetermined rotation axis R. Then, the engaging portion (sliding resistance generating portion) 52 and the engaged portion (sliding resistance generating portion) 62 of the lock mechanism 80 of the joint assembly 40 generates a sliding resistance around the predetermined rotation axis R between the housing 2 and the rotary element 6, when the central axis C is shifted relative to the predetermined rotation axis R. Herein, at a position closer to the end effector 5 than a support position where the shaft 3 of the rotary element 6 is supported by the supporting portion 51 of the housing 2, the joint assembly 40 generates a sliding resistance around the predetermined rotation axis R in the rotary element 6 (shaft 3). In addition, herein, the joint assembly 40 is adjacent to a support position (supported portion 61) supporting the shaft 3 of the rotary element 6 by the supporting portion 51 of the housing 2, and generates a sliding resistance in a direction around the predetermined rotation axis R with respect to the engaging portion 52 by the engaged portion 62 which is apart from the predetermined rotation axis R than the support position. That is, the sliding resistance around the predetermined rotation axis R is generated in the rotary element 6 (shaft 3). In this manner, the lock mechanism 80 can suppress the rotation of the rotary element 6 around the predetermined rotation axis R. Therefore, for example, when the external force F is applied to the end effector 5 arranged at a position deviated from the central axis C, rotation of the end effector 5 and the shaft 3 around the axis of the predetermined rotation axis R unintended by the operator can be effectively prevented by the lock mechanism 80.

On the other hand, when the operator intends to rotate the end effector 5 and the shaft 3 around the predetermined rotation axis R intentionally, the rotating knob 26A having the radius DO larger than the radius D1 of a portion generating the sliding resistance may be rotated. Thus, the operator can easily rotate the rotating knob 26A around the predetermined rotation axis R against the sliding resistance by the rotational moment.

In FIG. 5, an example has been described in which the recessed facing surface 63 facing the proximal end side of the engaged portion 62 of the rotating member 25 is in contact with the projection facing surface 53 facing the distal end side of the engaging portion 52 of the housing 2, when the central axis C of the shaft 3 is inclined with respect to the predetermined rotation axis R of the housing 2. Other than that, it is also preferable that the recessed facing surface 64 facing the distal end side of the engaged portion 62 of the rotating member 25 comes into contact with the projection facing surface 54 facing the proximal end side of the engaging portion 52 of the housing 2. In addition, it is also preferable that the recessed facing surface 63 facing the proximal end side of the engaged portion 62 of the rotating member 25 comes into contact with the projection facing surface 53 facing the distal end side of the engaging portion 52 of the housing 2, at the same time, the recessed facing surface 64 facing the distal end side of the engaged portion 62 of the rotating member 25 comes into contact with the projection facing surface 54 facing the proximal end side of the engaging portion 52 of the housing 2.

Herein, an example has been described in which the engagement projection 41 is formed in the housing 2, and the engagement recess 42 is formed in the rotating member 25 of the shaft 3. Although not shown, these may be opposite. Namely, it of course is preferable that the engagement recess 42 is formed in the housing 2, and the engagement projection 41 is formed in the connecting portion 26B of the rotating member 25.

First Modification

Figure 6:
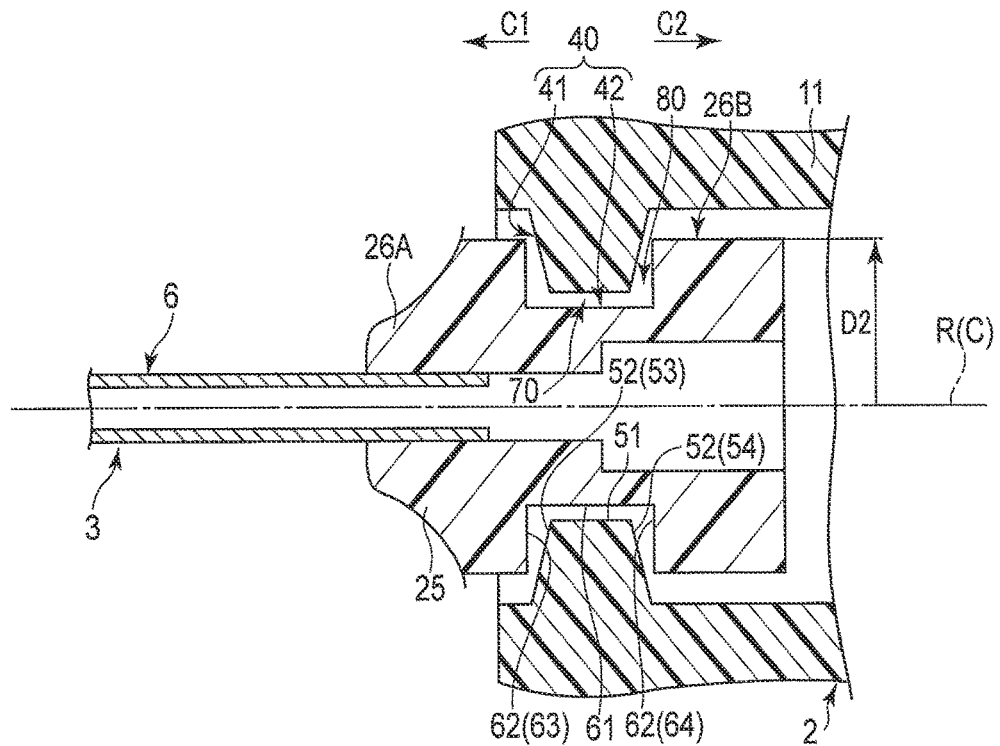
FIG. 6 is a schematic cross-sectional diagram showing a state in which a radius D2 of a connecting portion of the rotating member is made larger than a radius D1 shown in FIG. 4, in a treatment instrument according to a first modification of the first embodiment.
Figure 7:
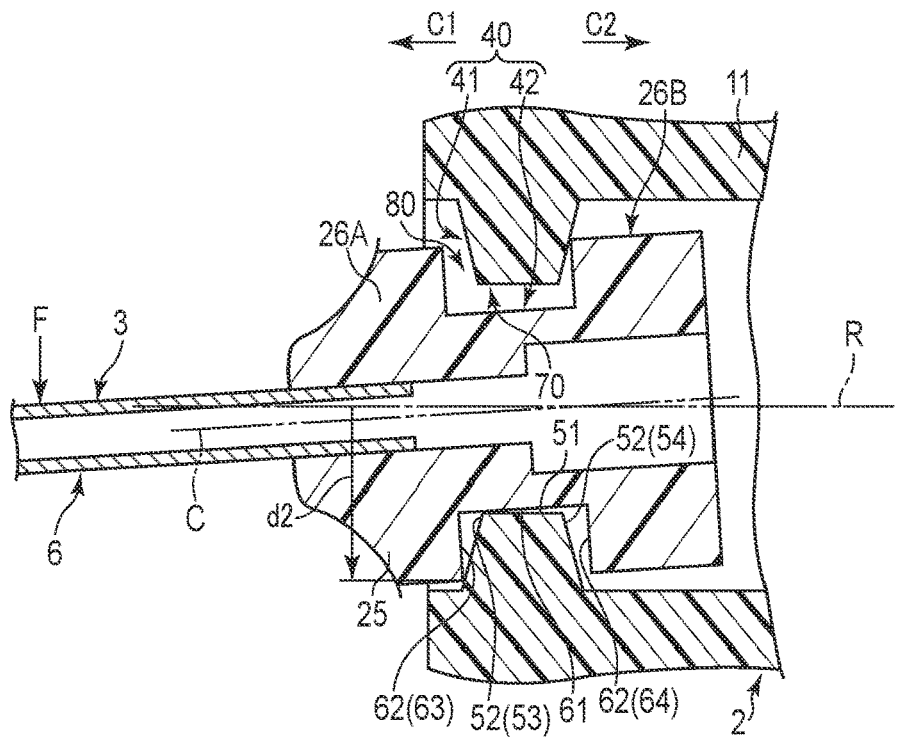
FIG. 7 is a schematic cross-sectional diagram showing a state in which the central axis of the shaft is shifted with respect to the predetermined rotation axis of the housing when the rotary element shown in FIG. 6 receives an external force from a direction deviated from the central axis, in the treatment instrument according to the first modification of the first embodiment.

A maximum radius D2 of the connecting portion 26B shown in FIG. 6 is formed larger than the maximum radius D1 (see FIG. 4) of the connecting portion 26B described in the first embodiment. As shown in FIG. 7, when the external force F is applied to the rotary element 6, the central axis C of the shaft 3 of the rotary element 6 is inclined with respect to the predetermined rotation axis R of the housing 2. A contact position (friction occurring position) between the recessed facing surface 63 of the engaged portion 62 and the projection facing surface 53 of the engaging portion 52 is at a position of a distance d2 (≥D2) with respect to the predetermined rotation axis R. The distance d2 is larger than the distance d1 (see FIG. 5) described in the first embodiment. Thus, in this modification, when the same external force F is applied to the same position of the end effector 5 and/or the shaft 3, it is possible to generate a larger rotational torque (sliding resistance) than the example described in the first embodiment. Therefore, an effect of suppressing the rotation around the predetermined rotation axis R in a state where the external force F is applied to the rotary element 6 can be higher in this modification than in the example described in the first embodiment.

Second Modification

This modification can be combined with the first embodiment and the first modification as appropriate.

Figure 8:
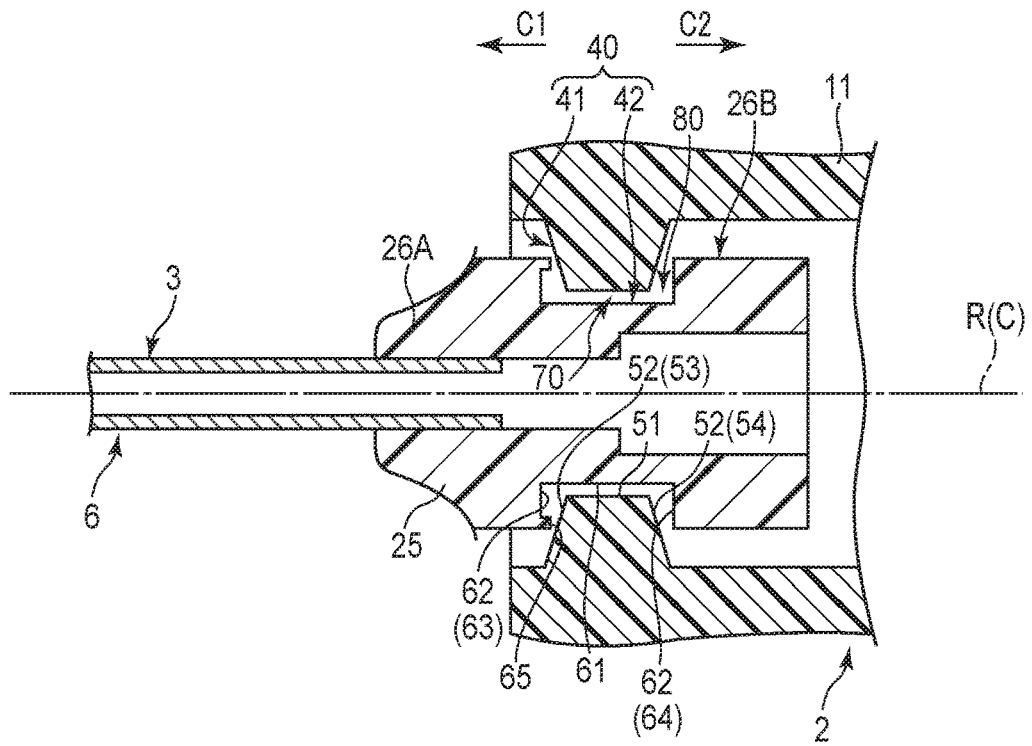
FIG. 8 is a schematic cross-sectional diagram showing a state in which a projection for effectively generating a frictional force against the housing is arranged in the rotating member, in a treatment instrument according to a second modification of the first embodiment.

As shown in FIG. 8, a protrusion 65 is formed on the recessed facing surface 63 of the engaged portion 62. The protrusion 65 protrudes toward the proximal end side from the recessed facing surface 63 of the engaged portion 62. It is preferable that the protrusion 65 is annularly formed around the central axis C. When the protrusion 65 is brought into contact with the projection facing surface 53 of the engaging portion 52, the contact is stronger for the protrusion than that of the recessed facing surface 63 of the engaged portion 62 described in the first embodiment. Therefore, in this modification, when the same external force F is applied to the same position of the end effector 5 and/or the shaft 3, as compared with the example (see FIG. 5) described in the first embodiment, it is possible to generate a large sliding resistance (frictional force) around the predetermined rotation axis R.

Third Modification

Figure 9:
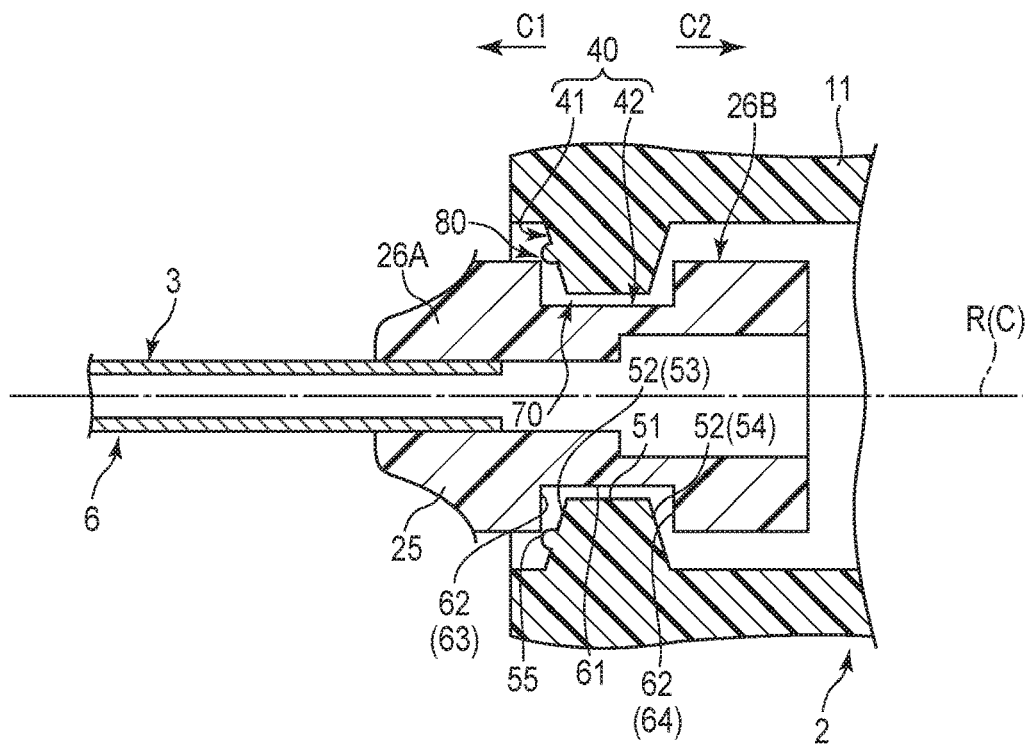
FIG. 9 is a schematic cross-sectional diagram showing a state in which a projection for effectively generating a frictional force against the rotating member is arranged in the housing, in a treatment instrument according to a third modification of the first embodiment.

As shown in FIG. 9, a protrusion 55 is formed on the projection facing surface 53 of the engaging portion 52 of the engagement recess 42. The protrusion 55 protrudes toward the recessed facing surface 63 of the engaged portion 62. It is preferable that the protrusion 55 is formed in an annular shape. Thus, when the protrusion 55 is brought into contact with the recessed facing surface 63 of the engaged portion 62 by the external force F to the rotary element 6, the contact is stronger for the protrusion than that of the projection facing surface 53 of the engaging portion 52 described in the first embodiment. Therefore, in this modification, when the same external force F is applied to the same position of the end effector 5 and/or the shaft 3, as compared with the example (see FIG. 5) described in the first embodiment, it is possible to generate a large sliding resistance (frictional force) around the predetermined rotation axis R.

Note that this modification can be appropriately combined with, for example, the first embodiment, the first modification, and the second modification.

Fourth Modification

As shown in FIG. 10, a friction plate 66 is fixed to the recessed facing surface 63 of the engaged portion 62. It is preferable that the friction plate 66 is formed in an annular shape. It is preferable that the friction plate 66 is made of a material having a large friction coefficient, such as a rubber material. The friction plate 66 protrudes toward the proximal end side from the recessed facing surface 63 of the engaged portion 62, and increases the frictional force when the projection facing surface 53 of the engaging portion 52 contacts. Thus, when the friction plate 66 is brought into contact with the projection facing surface 53 of the engaging portion 52, a larger frictional force is exhibited than the contact of the recessed facing surface 63 of the engaged portion 62 described in the first embodiment. Therefore, in this modification, when the same external force F is applied to the same position of the end effector 5 and/or the shaft 3, as compared with the example (see FIG. 5) described in the first embodiment, it is possible to generate a large sliding resistance (frictional force) around the predetermined rotation axis R.

This modification can be appropriately combined with, for example, the third modification.

Fifth Modification

As shown in FIG. 11, a friction plate 56 is fixed to the projection facing surface 53 of the engaging portion 52. It is preferable that the friction plate 56 is formed in an annular shape. The friction plate 56 increases the frictional force when the recessed facing surface 63 of the engaged portion 62 contacts. Thus, when the friction plate 56 is brought into contact with the recessed facing surface 63 of the engaged portion 62, a larger frictional force is exhibited than the contact of the projection facing surface 53 of the engaging portion 52 described in the first embodiment. Therefore, in this modification, when the same external force F is applied to the same position of the end effector 5 and/or the shaft 3, as compared with the example (see FIG. 5) described in the first embodiment, it is possible to generate a large sliding resistance (frictional force) around the predetermined rotation axis R.

This modification can be appropriately combined with, for example, the second modification.

Sixth Modification

Figure 12:
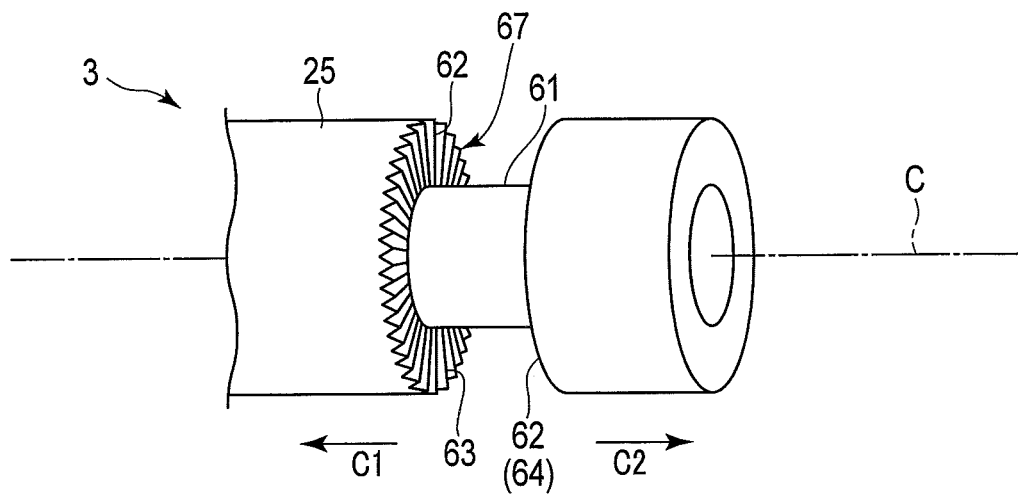
FIG. 12 is a schematic perspective diagram showing a state in which a large number of jagged steps are formed on the rotating member for effectively generating a frictional force with respect to the housing, in a treatment instrument according to a sixth modification of the first embodiment.

As shown in FIG. 12, multiple steps 67 are formed along a circumferential direction of the central axis C on the recessed facing surface 63 of the engaged portion 62. That is, the recessed facing surface 63 of the engaged portion 62 is formed in a jagged shape. Thus, when the recessed facing surface 63 of the engaged portion 62 is brought into contact with the projection facing surface 53 of the engaging portion 52, the projection facing surface 53 of the engaging portion 52 is hooked at a position protruding toward the proximal end side along the central axis C of the recessed facing surface 63 of the engaged portion 62. Therefore, in this modification, when the same external force F is applied to the same position of the end effector 5 and/or the shaft 3, it is possible to generate a large sliding resistance (frictional force) around the predetermined rotation axis R, as compared with the example (see FIG. 5) described in the first embodiment.

In FIG. 12, an example has been described in which the step 67 is formed on the recessed facing surface 63 of the engaged portion 62. Besides, the step 67 may be formed on the recessed facing surface 64 of the engaged portion 62. In addition, the step 67 may be formed on the projection facing surface 53 of the engaging portion (sliding resistance generating portion) 52, or may be formed on the projection facing surface 54 of the engaging portion 52.

Seventh Modification

Figure 13A:
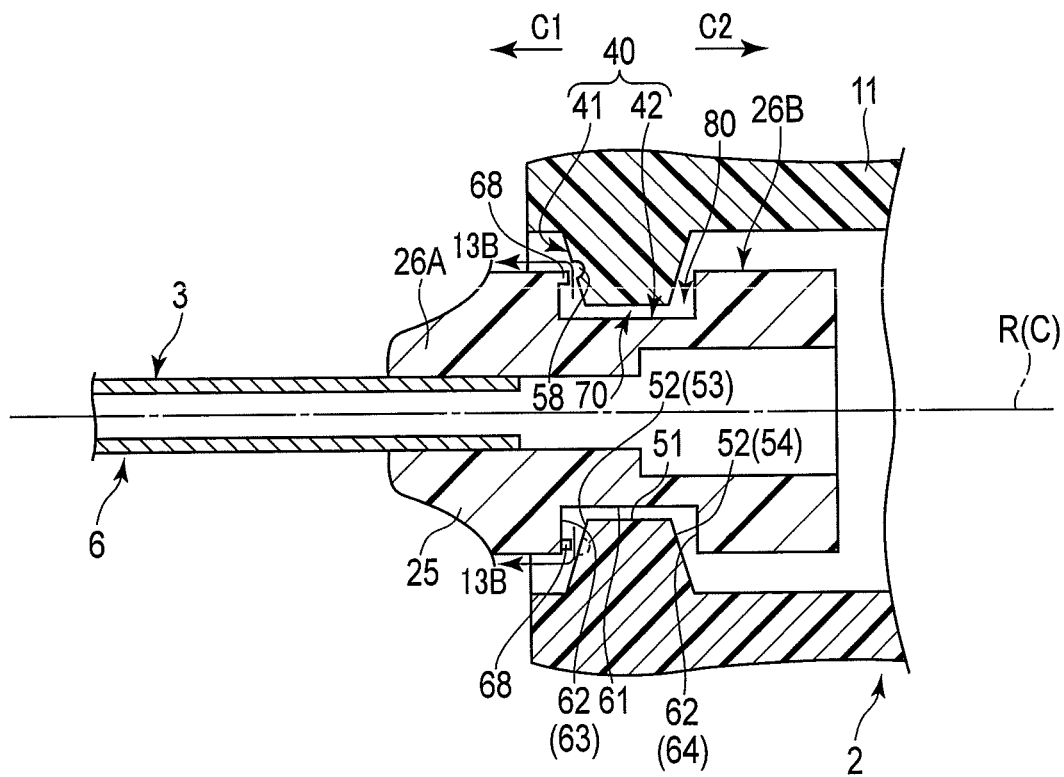
FIG. 13A is a schematic cross-sectional diagram showing a state in which a projection for effectively generating a frictional force with respect to the housing is arranged in the rotating member, and a recess fitted to a protrusion of the rotating member is arranged in the housing to effectively generate a frictional force with respect to the rotating member, in a treatment instrument according to a seventh modification of the first embodiment.
Figure 13B:
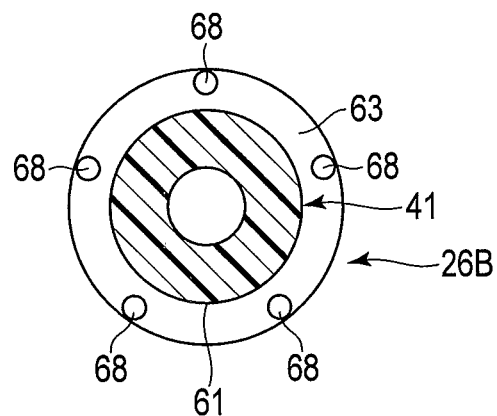
FIG. 13B is a schematic cross-sectional diagram as seen from a direction along line 13B-13B in FIG. 13A.

As shown in FIGS. 13A and 13B, on the recessed facing surface 63 of the engaged portion 62, one or more protrusions 68 are formed. Herein, five protrusions 68 are arranged at vertexes of a regular pentagon with respect to the central axis C. The protrusions 68 protrude from the recessed facing surface 63 of the engaged portion 62 toward the proximal end side along the central axis C.

As shown in FIG. 13A, a recess 58 is formed on the projection facing surface 53 of the engaging portion 52. The number of the recesses 58 may be the same as that of the protrusions 68, a larger number, or a smaller number.

The protrusion 68 can be fitted to the recess 58 at one or more positions. Thus, in this modification, when the same external force F is applied to the same position of the end effector 5 and/or the shaft 3, it is possible to generate a large sliding resistance (frictional force) around the predetermined rotation axis R, as compared with the example (see FIG. 5) described in the first embodiment.

Herein, an example has been described in which the protrusion 68 is formed on the recessed facing surface 63 of the engaged portion 62 and the recess 58 is formed on the projection facing surface 53 of the engaging portion 52, but these may of course be opposite.

Second Embodiment

Figure 14A:
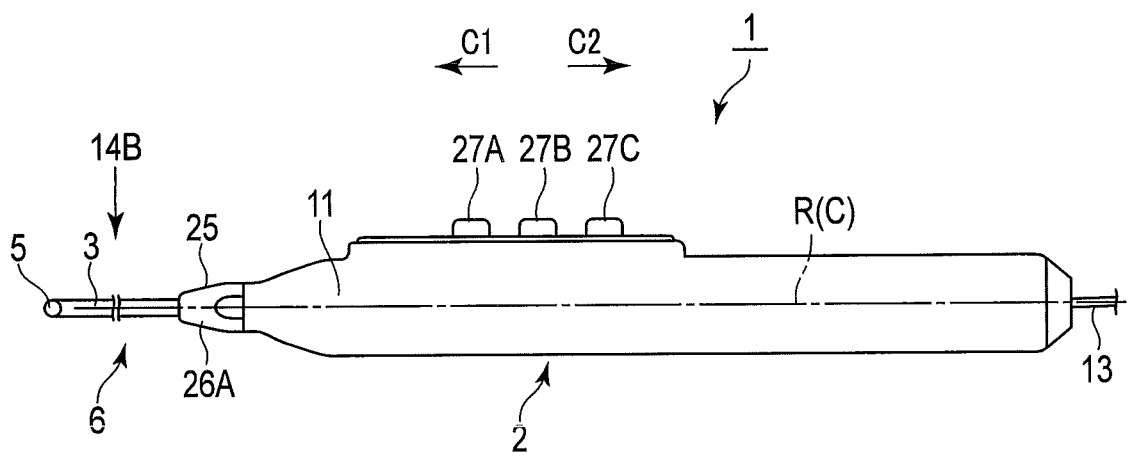
FIG. 14A is a schematic diagram showing a treatment instrument according to a second embodiment.
Figure 14B:
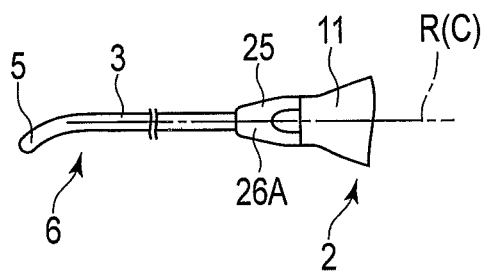
FIG. 14B is a schematic diagram showing a rotary element and a rotating member as seen from a direction indicated by an arrow 14B in FIG. 14A.

Next, a second embodiment will be described with reference to FIGS. 14A and 14B. This embodiment is a modification of the first embodiment including each modification, and the same members or members having the same function as those described in the first embodiment are denoted by the same reference numerals as much as possible, and a detailed description thereof will be omitted.

In the first embodiment including the first to seventh modifications, an example in which the end effector 5 can actively move at the distal end of the shaft 3 has been described. In addition, an example in which a pair of the grasping pieces 16 and 17 (see FIGS. 1 and 2) of the end effector 5 can be relatively opened and closed has been described. Herein, an example will be described in which the end effector 5 is formed integrally with the distal end of the shaft 3, and the end effector 5 is bent with respect to the shaft 3. That is, in the present embodiment, the end effector 5 is curved with respect to the shaft 3, and is located at a position shifted from the central axis C.

In the present embodiment, operation buttons 27A, 27B, and 27C are attached to the main body 11 of the housing 2. Each of the operation buttons 27A, 27B, and 27C is pressed to perform an operation input. When an operation input is performed with each of the operation buttons 27A, 27B, and 27C, the treatment instrument 1 is operated in a predetermined operation mode. At this time, for example, similarly to known treatment instruments, either one or more of high-frequency current, ultrasonic vibration, and heater heat is applied as a treatment energy to the treatment target with which the end effector 5 is in contact.

Even in this case, for example, in the same manner as shown in FIGS. 4 and 5 (or FIGS. 6 and 7), when the external force F is applied to the rotary element 6, the central axis C of the shaft 3 can be inclined with respect to the predetermined rotation axis R of the housing 2 to stop the rotation of the rotary element 6 relative to the housing 2. Thus, for example, when the external force F is applied to the end effector 5 arranged at a position deviated from the central axis C, rotation of the end effector 5 and the shaft 3 around the predetermined rotation axis R unintended by the operator can be effectively prevented by the lock mechanism 80.

On the other hand, when the operator operates the rotating knob 26A of the rotating member 25, for reasons of the rotational moment with respect to the predetermined rotation axis R against the frictional force between the housing 2 and the rotating member 25, for example, the rotating knob 26A can be rotated so as to push aside the living tissue by the end effector 5.

When the rotating member 25 is arranged in the internal portion of the housing main body 11, a structure (structure in which the shaft 3 is supported at a plurality of portions with respect to the housing 2) described in a third embodiment or a fourth embodiment can also be adopted.

Third Embodiment

Next, a third embodiment will be described with reference to FIGS. 15 to 17. This embodiment is a modification of the first embodiment including the first to seventh modifications and the second embodiment, and the same members or members having the same function as those described in the first and second embodiments are denoted by the same reference numerals as much as possible, and a detailed description thereof will be omitted.

In the first embodiment, an example in which the rotating member 25 is arranged at the distal end portion of the housing main body 11 has been described. Herein, as shown in FIG. 15, an example in which a part of the rotating knob 26A of the rotating member 25 protrudes from a side of the housing main body 11 will be described.

In the first embodiment, as shown in FIGS. 4 and 5, an example in which the rotating member 25 is supported at one position with respect to the housing main body 11 has been described. That is, in the first embodiment, an example in which the treatment instrument 1 includes one joint assembly 40 has been described. Herein, as shown in FIG. 16, an example in which the rotating member 25 is supported at two positions (a plurality of positions) with respect to the housing main body 11 will be described. That is, in the present embodiment, an example in which the treatment instrument 1 includes a first joint (joint assembly) 140 and a second joint (joint assembly) 240 will be described.

In the present embodiment, the rotating member 25 includes a rotating knob 26A, the first connecting portion (proximal end side connecting portion) 26B and a second connecting portion (distal end side connecting portion) 26C.

As shown in FIG. 16, the housing main body 11 is formed with openings 11A and 11B through which the rotating knob 26A protrudes. It is preferable that the openings 11A and 11B are formed on a side surface of the housing main body 11 shown in FIG. 15. In the housing 2, a first engagement projection 141 is formed on the proximal end side along the predetermined rotation axis R with respect to the openings 11A and 11B. In the housing 2, a second engagement projection 241 is formed on the distal end side along the predetermined rotation axis R with respect to the openings 11A and 11B.

A first engagement recess 142 engaging with the first engagement projection 141 of the housing 2 is formed on the outer peripheral surface of the first connecting portion 26B of the rotating member 25. The first engagement projection 141 and the first engagement recess 142 constitute the first joint (joint assembly) 140. A second engagement recess 242 engaging with the second engagement projection 241 of the housing 2 is formed on an outer peripheral surface of the second connecting portion 26C of the rotating member 25. The second engagement projection 241 and the second engagement recess 242 constitute the second joint (joint assembly) 240.

Herein, for simplicity of explanation, it is assumed that the maximum radius of the first connecting portion 26B is the same as that of the second connecting portion 26C, which is D1. The maximum radius D1 of the first connecting portion 26B and the second connecting portion 26C is smaller than the maximum radius D0 of the rotating knob 26A.

An opening 2A through which the shaft 3 passes is formed at the distal end of the housing main body 11. The opening 2A has an inner diameter larger than the outer diameter of the shaft 3 so as to allow the shaft 3 to bend appropriately. Thus, the shaft 3, i.e., the rotary element 6 can bend relative to the central axis C by the external force F from a direction deviated from the predetermined rotation axis R.

The engagement projection 141 of the housing 2 includes a supporting portion (rotation supporting surface) 151 and an engaging portion 152. The supporting portion 151 defines a cylindrical inner peripheral surface with respect to the predetermined rotation axis R. The engaging portion 152 is adjacent to the supporting portion 151 along the predetermined rotation axis R. The engaging portion 152 includes a projection facing surface (first receiving surface) 153 facing the distal end side and a projection facing surface (second receiving surface) 154 facing the proximal end side.

The engagement recess 142 of the rotary member 25 of a part of the shaft 3 includes a supported portion (rotation supporting surface) 161 and an engaged portion 162. The supported portion 161 defines a cylindrical outer peripheral surface with respect to the central axis C. The engaged portion 162 is adjacent to the supported surface 161 along the central axis C. The engaged portion 162 includes a recessed facing surface (first contact surface) 163 facing the proximal end side and a recessed facing surface (second contact surface) 164 facing the distal end side.

In the present embodiment, the supporting portion 151 of the housing 2 and the supported portion 161 of the shaft 3 cooperate to form a rotation supporting mechanism 170. The engaging portion 152 of the housing 2 and the engaged portion 162 of the shaft 3 cooperate to form a lock mechanism 180.

Between the projection facing surface 153 of the engaging portion 152 and the recessed facing surface 163 of the engaged portion 162, and/or between the projection facing surface 154 of the engaging portion 152 and the recessed facing surface 164 of the engaged portion 162, a sliding resistance (friction) can be generated by an inclination of the central axis C of the shaft 3 of the rotary element 6 with respect to the predetermined rotation axis R.

Figure 17:
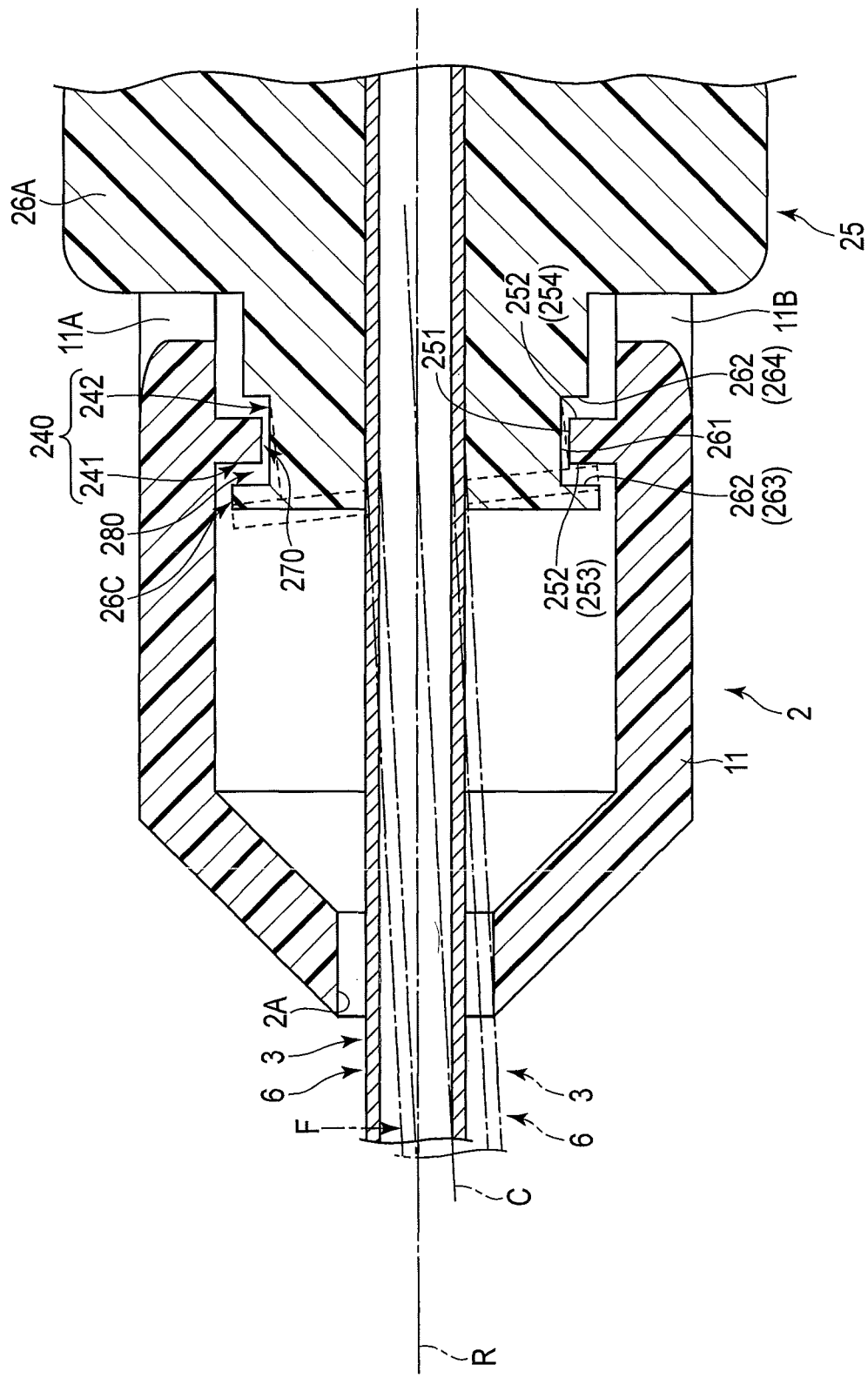
FIG. 17 is a schematic cross-sectional diagram showing a state in which the central axis of the shaft coincides with the predetermined rotation axis of the housing is indicated by a solid line, and a state in which the central axis of the shaft is shifted with respect to the predetermined rotation axis of the housing when a rotary element receives an external force from a direction deviated from the central axis, in the treatment instrument according to the third embodiment.

As shown in FIG. 17, the engagement projection 241 of the housing 2 includes a supporting portion (rotation supporting surface) 251 and an engaging portion 252. The supporting portion 251 defines a cylindrical inner peripheral surface with respect to the predetermined rotation axis R. The engaging portion 252 is adjacent to the supporting portion 251 along the central axis C. The engaging portion 252 includes a projection facing surface (first receiving surface) 253 facing the distal end side and a projection facing surface (second receiving surface) 254 facing the proximal end side.

The engagement recess 242 of the rotating member 25 of a part of the shaft 3 includes a supported portion (rotation supporting surface) 261 and an engaged portion 262. The supported portion 261 defines a cylindrical outer peripheral surface with respect to the central axis C. The engaged portion 262 is adjacent to the supported surface 261 along the central axis C. The engaged portion 262 includes a recessed facing surface (first contact surface) 263 facing the proximal end side and a recessed facing surface (second contact surface) 264 facing the distal end side.

Between the projection facing surface 253 of the engaging portion 252 and the recessed facing surface 263 of the engaged portion 262, and/or between the projection facing surface 254 of the engaging portion 252 and the recessed facing surface 264 of the engaged portion 262, a sliding resistance (friction) can be generated by the inclination of the central axis C of the shaft 3 of the rotary element 6 with respect to the predetermined rotation axis R.

In the present embodiment, the supporting portion 251 of the housing 2 and the supported portion 261 of the shaft 3 cooperate to form a rotation supporting mechanism 270. The engaging portion 252 of the housing 2 and the engaged portion 262 of the shaft 3 cooperate to form a lock mechanism 280.

In the rotation supporting mechanism 170, the supporting portion 151 of the engagement projection 141 of the housing 2 cooperates with the supported portion 161 of the engagement recess 142 of the shaft 3 to make the central axis C of the shaft 3 coincide with the predetermined rotation axis R of the housing main body 11 of the housing 2. In the rotation supporting mechanism 270, the supporting portion 251 of the engagement projection 241 of the housing 2 cooperates with the supported portion 261 of the engagement recess 242 of the shaft 3 to make the central axis C of the shaft 3 coincide with the predetermined rotation axis R of the housing main body 11 of the housing 2. Herein, it is preferable that the first joint 140 is formed with less rattling than the second joint 240.

As shown in FIG. 17, when the external force F is received from a position deviated from the central axis C with respect to the rotary element 6, the shaft 3 is elastically deformed and bent as indicated by a broken line in FIG. 17, and the rotating member 25 is elastically deformed relative to the main body 11 of the housing 2. At this time, an amount of deformation of the rotating member 25 is larger at the second connecting portion 26C having a short distance to a point of application of the external force F than at the first connecting portion 26B having a long distance to the point of application of the external force F. Thus, a deviation of the central axis C of the shaft 3 with respect to the predetermined rotation axis R of the housing 2 is greater at the second connecting portion 26C than at the first connecting portion 26B.

The treatment instrument 1 of the present embodiment supports the shaft 3 with respect to the housing 2 at two positions (joints 140, 240) along the predetermined rotation axis R. Thus, as compared with the example (see FIG. 5) in which the shaft 3 is supported at one position (joint assembly 40) with respect to the housing 2 described in the first embodiment, it is possible to make it difficult to incline the shaft 3. On the other hand, the shaft 3 has a bendability which can shift the rotary element 6 with respect to the predetermined rotation axis R of the housing 2 due to the elastic deformation by a load of the external force F applied to the rotary element 6 from a direction deviated from the predetermined rotation axis R. For this reason, the central axis C of the shaft 3 is shifted with respect to the predetermined rotation axis R by the bending of the shaft 3 with respect to the housing 2.

Due to the elastic deformation of the second connecting portion 26C of the rotating member 25, the recessed facing surface 263 of the engaged portion (sliding resistance generating portion) 262 of the engagement recess (supported portion) 242 of the rotating member 25 contacts the projection facing surface 253 of the engaging portion 252 of the engagement projection 241 of the housing 2. For this reason, sliding resistance between the housing 2 and the rotating member 25 is generated in the same manner as described in the first embodiment. Accordingly, even if the external force F is applied to the rotary element 6 as indicated by broken lines in FIG. 17 and a force to rotate the end effector 5 and/or the shaft 3 around the central axis C is applied, a braking action for suppressing rotation relative to the housing 2 continues to be generated in the rotating member 25. As the external force F increases, the recessed facing surface 263 of the engaged portion 262 of the rotating member 25 strongly contacts the projection facing surface 253 of the engaging portion 252 of the housing 2. Thus, as the external force F increases, the braking action (sliding resistance) around the rotation axis R of the housing 2 against the rotation member 25 also increases.

Therefore, rotation of the shaft 3 around the central axis C of the shaft 3 is suppressed along with the unintentional rotation of the rotating member 25 relative to the housing 2 being suppressed, and furthermore, the rotation of the end effector 5 around the central axis C is suppressed. When the external force F is applied to the end effector 5 arranged at a position deviated from the central axis C, for example, rotation of the end effector 5 and the shaft 3 around the predetermined rotation axis R unintended by the operator can be effectively prevented by the lock mechanism 280.

On the other hand, when the operator intends to rotate the end effector 5 and the shaft 3 around the predetermined rotation axis R intentionally, the rotating knob 26A having the radius D0 larger than the radius D1 of a portion generating the sliding resistance may be rotated. Thus, the operator can easily rotate the rotating knob 26A around the predetermined rotation axis R against the sliding resistance by the rotational moment. Therefore, for example, the operator can push aside the living tissue by turning the end effector 5, which is at a position deviated from the central axis C, around the central axis C. When the operator rotates the rotating member 25 against the frictional force (sliding resistance), the central axis C of the shaft 3 tries to move to coincide with the predetermined rotation axis R of the housing 2 so as to avoid generation of friction between the engaging portion 252 and the engaged portion 262.

For example, it is a matter of course that when the external force F is applied to the end effector 5 arranged at a position deviated from the central axis C, depending on the magnitude of the external force F, the lock mechanism 180 can also cooperate with the lock mechanism 280 to exert the function of preventing rotation of the end effector 5 and the shaft 3 around the predetermined rotation axis R unintended by the operator.

First Modification

As shown in FIG. 18, a friction ring 2B is formed on an inner peripheral surface of the opening 2A at the distal end of the main body 11 of the housing 2.

Thus, when the outer peripheral surface of the shaft 3 is brought into contact with the friction ring 2B, it is possible to suppress unintentional rotation of the shaft 3 around the predetermined rotation axis R due to the external force F in cooperation with the lock mechanism 280 (and the lock mechanism 180).

Second Modification

In this modification, an example in which the shaft 3 is supported by the housing 2 at a position apart from the rotating member 25 to exert the braking action on the shaft 3 will be described.

Figure 19:
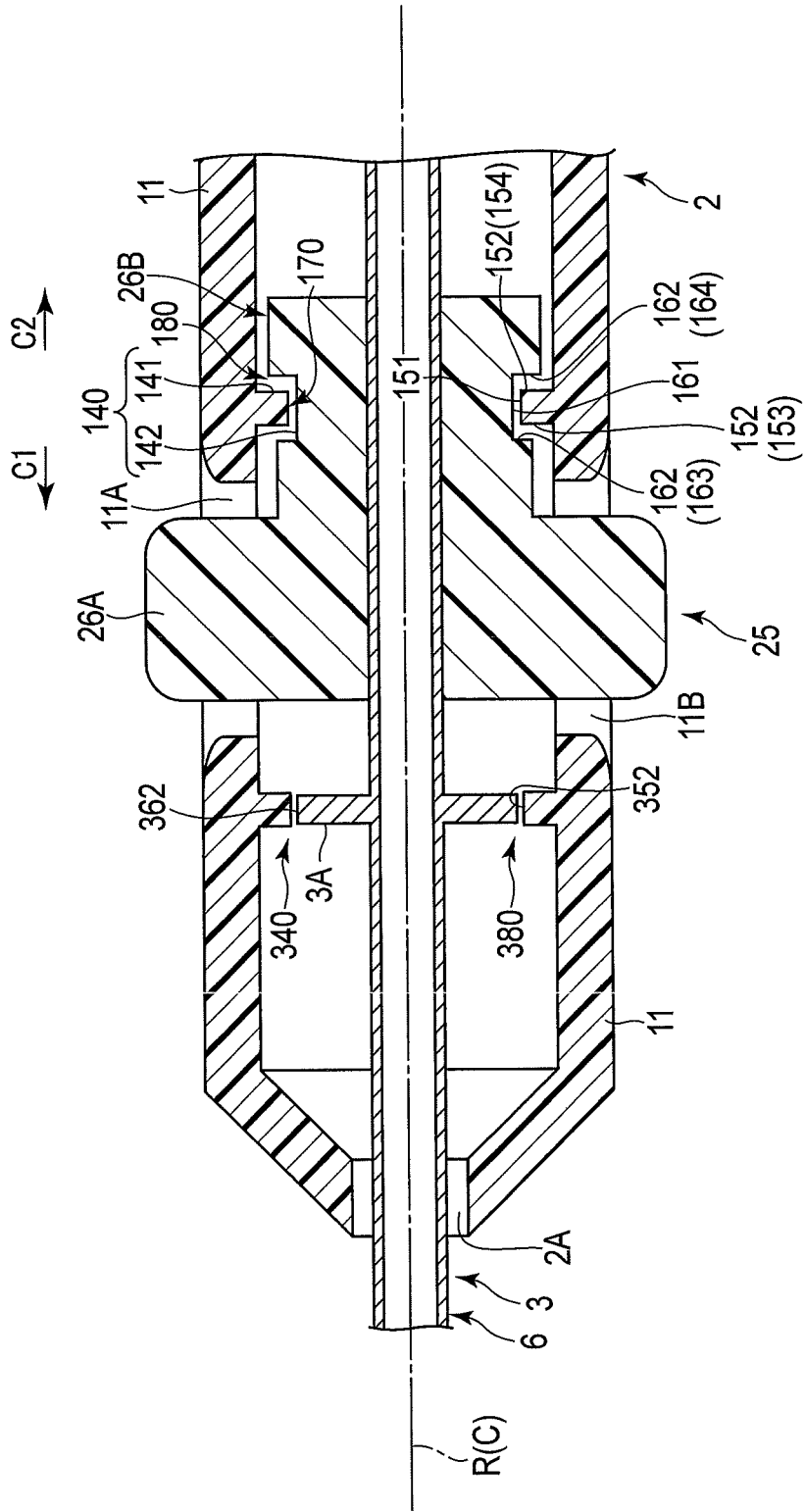
FIG. 19 is a schematic cross-sectional diagram showing a state in which the central axis of the shaft coincides with the predetermined rotation axis of the housing, in a treatment instrument according to a second modification of the third embodiment.

As shown in FIGS. 19 and 20, in the present modification, a joint (joint assembly) 340 prepared by deforming the structure of the second joint (joint assembly) 240 is formed.

On the inner peripheral surface of the main body 11 of the housing 2, an engagement projection 341 facing an outer peripheral surface of a flange 3A is formed. An engaging portion 352 generating a frictional force is formed on an inner peripheral surface of the engagement projection 341 with respect to the predetermined rotation axis R.

On the outer peripheral surface of the shaft 3, the flange 3A protruding outward in the radial direction with respect to the central axis C is formed. An outer diameter of the flange 3A is smaller than an inner diameter of the engaging portion 352 of the engagement projection 341 of the housing 2. The outer peripheral surface of the flange 3A is processed or coated so as to generate an appropriate friction between with the engaging portion 352 to be described later. In the present embodiment, the engaging portion 352 of the housing 2 and an engaged portion 362 on the outer peripheral surface of the flange 3A of the shaft 3 cooperate to form a lock mechanism 380.

As shown in FIG. 20, when receiving the external force F from a position deviated from the central axis C with respect to the rotary element 6, the shaft 3 elastically deforms as indicated by broken lines in FIG. 20. The engaged portion (sliding resistance generating portion) 362 of the shaft 3 comes into contact with the engaging portion 352 of the housing 2. Thus, a sliding resistance is generated between the housing 2 and the flange 3A of the shaft 3 in the same manner as described above.

Therefore, for example, when the external force F is applied to the end effector 5 arranged at a position deviated from the central axis C, rotation of the end effector 5 and the shaft 3 around the predetermined rotation axis R can be effectively prevented by the lock mechanism 380.

For example, when the external force F is applied to the end effector 5 arranged at a position deviated from the central axis C, depending on the magnitude of the external force F, the lock mechanism 180 can also cooperate with the lock mechanism 380 to exert the function of preventing the rotation of the end effector 5 and the shaft 3 around the predetermined rotation axis R unintended by the operator.

Fourth Embodiment

Next, a fourth embodiment will be described with reference to FIGS. 21 and 22. This embodiment is a modification of the first to third embodiments including each modification, and the same members or members having the same function as those described in the first to third embodiments are denoted by the same reference numerals as much as possible, and a detailed description thereof will be omitted.

In the treatment instrument 1 described in the first embodiment, as shown in FIG. 4, an example in which the engagement projection 41 is formed in the housing 2, and the engagement recess 42 is formed in the rotating member 25 has been described. In the present embodiment, as shown in FIG. 21, an example will be described in which engagement recesses 442 and 542 are formed in the housing 2, and engagement projections 441 and 541 are formed in the rotating member 25. The rotating member 25 includes a rotating knob 26A, a first connecting portion (proximal end side connecting portion) 26D, and a second connecting portion (distal end side connecting portion) 26E.

As shown in FIG. 21, the treatment instrument 1 includes a first joint (joint assembly) 440 and a second joint (joint assembly) 540.

The first joint 440 includes the engagement projection (supporting portion) 441 and the engagement recess (supported portion) 442.

The engagement projection (supporting portion) 441 protruding toward the inner peripheral side is provided in the first connecting portion 26D of the rotating member 25. As an example, the engagement projection (inner flange) 441 is provided over an entire circumference around the central axis C of the shaft 3. Although not shown, the engagement projection 441 may be formed, for example, at appropriate intervals in a circumferential direction around the central axis C of the shaft 3. Thus, one engagement projection 441 may be provided, or a plurality of engagement projections 441 may be provided.

On the outer peripheral surface of the main body 11 of the housing 2, an engagement recess (supported portion) 442 that is recessed toward the inner peripheral side is provided. The engagement recess 442 is provided over the entire circumference around the rotation axis R. By the engagement projection 441 being engaged with the engagement recess 442, the shaft 3 is supported by the housing 2 so as to be rotatable around the predetermined rotation axis R.

Thus, the engagement projection 441 can move around the predetermined rotation axis R relative to the engagement recess 442. The rotating member 25 of the shaft 3 is rotatable around the predetermined rotation axis R relative to the housing 2. Therefore, the engagement projection 441 and the engagement recess 442 form a joint assembly (connecting portion) 440 that connects the shaft 3 so as to be rotatable around the predetermined rotation axis R of the housing 2.

As shown in FIG. 21, the engagement projection 441 of the rotating member 25 includes a supporting portion (rotation supporting surface) 451 and an engaging portion (sliding resistance generating portion) 452. The supporting portion 451 defines a cylindrical inner peripheral surface with respect to the central axis C of the shaft 3. The engaging portion 452 is adjacent to the supporting portion 451 along the central axis C. The engaging portion 452 includes a projection facing surface (first receiving surface) 453 facing the distal end side and a projection facing surface (second receiving surface) 454 facing the proximal end side.

The engagement recess 442 on the outer peripheral surface of the housing 2 includes a supported portion (rotation supporting surface) 461 and an engaged portion (sliding resistance generating portion) 462. The supported portion 461 defines a cylindrical outer peripheral surface with respect to the predetermined rotation axis R. The engaged portion 462 is adjacent to the supported surface 461 along the rotation axis R. The engaged portion 462 includes a recessed facing surface (first contact surface) 463 facing the proximal end side and a recessed facing surface (second contact surface) 464 facing the distal end side.

The recessed facing surface (first contact surface) 463 facing the proximal end side of the engagement recess 442 faces the projection facing surface (first receiving surface) 453 facing the distal end side of the engagement projection 441. The recessed facing surface (second contact surface) 464 facing the distal end side of the engagement recess 442 faces the projection facing surface (second receiving surface) 454 facing the proximal end side of the engagement projection 441.

The projection facing surface 453 of the engagement projection 441 and the recessed facing surface 463 of the engagement recess 442, and the projection facing surface 454 of the engagement projection 441 and the recessed facing surface 464 of the engagement recess 442, each, are formed so as to generate a large frictional force when in contact, as compared with the frictional force (sliding resistance) between the supporting portion 451 and the supported portion 461.

In the present embodiment, the supporting portion 451 of the housing 2 and the supported portion 461 of the shaft 3 cooperate to form a rotation supporting mechanism 470. The engaging portion 452 of the housing 2 and the engaged portion 462 of the shaft 3 cooperate to form a lock mechanism 480.

The second joint 540 includes the engagement projection (supporting portion) 541 and the engagement recess (supported portion) 542.

As shown in FIG. 22, the engagement projection (supporting portion) 541 protruding toward the inner peripheral side is provided in the second connecting portion 26E of the rotating member 25. As an example, the engagement projection (inner flange) 541 is provided over the entire circumference around the central axis C of the shaft 3. Although not shown, the engagement projection 541 may be formed, for example, at appropriate intervals in the circumferential direction around the central axis C of the shaft 3. Thus, one engagement projection 541 may be provided, or a plurality of engagement projections 541 may be provided.

On the outer peripheral surface of the main body 11 of the housing 2, the engagement recess (supported portion) 542 that is recessed toward the inner peripheral side is provided. The engagement recess 542 is provided over the entire circumference around the rotation axis R. By the engagement projection 541 being engaged with the engagement recess 542, the shaft 3 is supported by the housing 2 so as to be rotatable around the predetermined rotation axis R.

Thus, the engagement projection 541 can move around the predetermined rotation axis R relative to the engagement recess 542. The rotating member 25 of the shaft 3 is rotatable around the predetermined rotation axis R relative to the housing 2. Accordingly, the engagement projection 541 and the engagement recess 542 form the joint (connecting portion) 540 that connects the shaft 3 so as to be rotatable around the predetermined rotation axis R of the housing 2.

The engagement projection 541 of the rotating member 25 includes a supporting portion (rotation supporting surface) 551 and an engaging portion (sliding resistance generating portion) 552. The supporting portion 551 defines a cylindrical inner peripheral surface with respect to the central axis C of the shaft 3. The engaging portion 552 is adjacent to the supporting portion 551 along the central axis C. The engaging portion 552 includes a projection facing surface (first receiving surface) 553 facing the distal end side and a projection facing surface (second receiving surface) 554 facing the proximal end side.

The engagement recess 542 on the outer peripheral surface of the housing 2 includes a supported portion (rotation supporting surface) 561 and an engaged portion (sliding resistance generating portion) 562. The supported portion 561 defines a cylindrical outer peripheral surface with respect to the predetermined rotation axis R. The engaged portion 562 is adjacent to the supported surface 561 along the rotation axis R. The engaged portion 562 includes a recessed facing surface (first contact surface) 563 facing the proximal end side and a recessed facing surface (second contact surface) 564 facing the distal end side.

The recessed facing surface (first contact surface) 563 facing the proximal end side of the engagement recess 542 faces the projection facing surface (first receiving surface) 553 facing the distal end side of the engagement projection 541. The recessed facing surface (second contact surface) 564 facing the distal end side of the engagement recess 542 faces the projection facing surface (second receiving surface) 554 facing the proximal end side of the engagement projection 552.

The projection facing surface 553 of the engagement projection 541 and the recessed facing surface 563 of the engagement recess 542, and the projection facing surface 554 of the engagement projection 541 and the recessed facing surface 564 of the engagement recess 542, each, are formed so as to generate a large frictional force when in contact, as compared with the frictional force (sliding resistance) between the supporting portion 551 and the supported portion 561.

The engaging portion 552 is at a position adjacent to the distal end side and the proximal end side of the supporting portion 551. Thus, a position of the supporting portion 551 and that of the engaging portion 552 are different from each other. Similarly, the engaged portion 562 is at a position adjacent to the distal end side and the proximal end side of the supported portion 561. Thus, a position of the supported portion 561 and that of the engaged portion 562 are different from each other.

The supporting portion 551 of the housing 2 and the supported portion 561 of the shaft 3 cooperate to form a rotation supporting mechanism 570. The engaging portion 552 of the housing 2 and the engaged portion 562 of the shaft 3 cooperate to form a lock mechanism 580.

In the rotation supporting mechanism 470, the supporting portion 451 of the engagement projection 441 of the housing 2 cooperates with the supported portion 461 of the engagement recess 442 of the shaft 3 to make the central axis C of the shaft 3 coincide with the predetermined rotation axis R of the housing main body 11 of the housing 2. In addition, in the rotation supporting mechanism 570, the supporting portion 551 of the engagement projection 541 of the housing 2 cooperates with the supported portion 561 of the engagement recess 542 of the shaft 3 to make the central axis C of the shaft 3 coincide with the predetermined rotation axis R of the housing main body 11 of the housing 2.

The supporting portion 551 of the engagement projection 541 of the rotating member 25 cooperates with the supported portion 561 of the engagement recess 542 of the housing 2 to make the central axis C of the shaft 3 coincide with the predetermined rotation axis R of the housing main body 11 of the housing 2. Herein, an inner diameter of the supporting portion 551 with respect to the central axis C is formed to be larger than an outer diameter of the supported portion 561 with respect to the predetermined rotation axis R. Thus, the supporting portion 551 of the engagement projection 541 of the rotating member 25 is rattled, that is, plays with respect to the supported portion 561 of the engagement recess 542 of the housing 2. For this reason, for example, when an external force from a position deviated from the central axis C of the shaft 3 is applied to the rotary element 6, the central axis C of the shaft 3 is displaced from the predetermined rotation axis R of the housing 2, from a position indicated by a solid line to a position indicated by a broken line in FIG. 22.

Herein, the treatment instrument 1 of the present embodiment supports the shaft 3 with respect to the housing 2 at two positions (joints 440, 540) along the predetermined rotation axis R. Thus, as compared with the example (see FIG. 5) in which the shaft 3 is supported at one position (joint assembly 40) with respect to the housing 2 described in the first embodiment, it is possible to make it difficult to incline the shaft 3. On the other hand, the shaft 3 has a bendability which can displace the rotary element 6 with respect to the predetermined rotation axis R of the housing 2 due to the elastic deformation by a load of the external force F applied to the rotary element 6 from a direction deviated from the predetermined rotation axis R. For this reason, the central axis C of the shaft 3 is displaced with respect to the predetermined rotation axis R by the bending of the shaft 3 relative to the housing 2.

At this time, the rotation of the rotary element 6 around the predetermined rotation axis R can be suppressed by the lock mechanism 580. More specifically, the lock mechanism 580 can suppress the rotation of the rotary element 6 around the predetermined rotation axis R at a position different from that of the supporting portion 551. Accordingly, for example, when the external force F is applied to the end effector 5 arranged at a position deviated from the central axis C, rotation of the end effector 5 and the shaft 3 around the predetermined rotation axis R unintended by the operator can be effectively prevented by the lock mechanism 580.

When the operator intends to rotate the end effector 5 and the shaft 3 around the predetermined rotation axis R intentionally, the rotating knob 26A having the radius DO larger than the maximum radius D3 with respect to the predetermined rotation axis R in the main body 11 of the housing 2 may be rotated. Thus, the operator can easily rotate the rotating knob 26A around the predetermined rotation axis R against the sliding resistance by the rotational moment.

For example, when the external force F is applied to the end effector 5 arranged at a position deviated from the central axis C, depending on the magnitude of the external force, the lock mechanism 480 can also cooperate with the lock mechanism 580 to effectively prevent rotation of the end effector 5 and the shaft 3 around the predetermined rotation axis R unintended by the operator.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
    a rotating body including:
        a shaft that extends along a longitudinal axis from a proximal end to a distal end;
        an end effector that is disposed at the distal end of the shaft; and
        a connecting portion that is attached to the shaft; and
    a housing that is configured to support the rotating body such that the rotating body is rotatable around a predetermined rotation axis with respect to the housing, wherein:
    one of the connecting portion and the housing includes an engagement projection that protrudes in a direction traverse to the predetermined rotation axis, and a different one of the connecting portion and the housing includes an engagement recess that is recessed in the direction transverse to the predetermined rotation axis and extends entirely around the predetermined rotation axis,
    the engagement projection is configured to rotate around the predetermined rotation axis relative to the engagement recess in a state in which the engagement projection is disposed in the engagement recess,
    the engagement projection includes a first rotation support surface and a first sliding resistance surface,
    the engagement recess includes a second rotation support surface that faces the first rotation support surface, and a second sliding resistance surface that faces the first sliding resistance surface,
    when the longitudinal axis deviates from the predetermined rotation axis, the first sliding resistance surface is configured to come into contact with the second sliding resistance surface to generate a frictional force that is larger than a frictional force generated between the first rotation support surface and the second rotation support surface when the first rotation support surface and the second rotation support surface come into contact with each other, and
    the first sliding resistance surface and the second sliding resistance surface are transverse to the longitudinal axis, and the first rotation support surface and the second rotation support surface are parallel to the longitudinal axis in a state in which the longitudinal axis is not deviated from the predetermined rotation axis.

2. The treatment instrument according to claim 1, wherein a distance from the predetermined rotation axis to the second sliding resistance surface is greater than a distance from the predetermined rotation axis to the first rotation support surface.

3. The treatment instrument according to claim 1, wherein, between the first rotation support surface and the second rotation support surface, there is a play that is configured to displace the rotating body with respect to the predetermined rotation axis of the housing by a load of an external force applied to the rotating body from a direction transverse to the predetermined rotation axis.

4. The treatment instrument according to claim 1, wherein:
    an opening through which the shaft passes is formed at a distal end of the housing, and
    an inner diameter of the opening is larger than an outer diameter of the shaft.

5. The treatment instrument according to claim 1, wherein:
    the engagement projection and the engagement recess form a joint assembly that is rotatable around the predetermined rotation axis.

6. The treatment instrument according to claim 5, wherein the engagement projection includes a plurality of parts at appropriate intervals in a circumferential direction around the predetermined rotation axis.

7. The treatment instrument according to claim 5, wherein the joint assembly includes a plurality of joints on the rotating body and the housing.

8. The treatment instrument according to claim 7, wherein:
the joint assembly includes a first joint and a second joint,
the first joint is arranged at a proximal side of the second joint along the longitudinal axis, and
the first joint is formed with less rattling than the second joint.

9. The treatment instrument according to claim 7, wherein:
the rotating body includes a rotating knob configured to be operated, and
a clearance along the longitudinal axis between the housing and the rotating knob is larger than a clearance of the joint assembly between the engagement projection and the engagement recess along the longitudinal axis.

10. The treatment instrument according to claim 7, wherein:
the rotating body includes a rotating knob configured to be operated, and
a clearance along a direction perpendicular to the longitudinal axis between the housing and the rotating knob is larger than a clearance along the direction perpendicular to the longitudinal axis of the joint assembly between the engagement projection and the engagement recess.

11. The treatment instrument according to claim 1, wherein:
the rotating body includes a rotating knob configured to be operated, and
a maximum radius of the rotating knob is larger than a maximum radius of the connecting portion.

12. The treatment instrument according to claim 1, wherein the shaft of the rotating body is configured to be elastically deformed.

13. The treatment instrument according to claim 1, further comprising an operation element attached to the housing and configured to be rotationally operated,
wherein the end effector is configured to bend with respect to the shaft by an operation of the operation element.

14. The treatment instrument according to claim 1, wherein the first sliding resistance surface and the second sliding resistance surface are transverse to the longitudinal axis in the state in which the longitudinal axis is not deviated from the predetermined rotation axis.

15. The treatment instrument according to claim 1, wherein the first sliding resistance surface and the second sliding resistance surface:
extend in a direction transverse to the longitudinal axis in the state in which the longitudinal axis is not deviated from the predetermined rotation axis, and
are formed of a material that generates an increased frictional force when the first sliding resistance surface and the second sliding resistance surface are in contact with each other or are subjected to surface processing so as to generate an increased frictional force when the first sliding resistance surface and the second sliding resistance surface are in contact with each other.

16. A treatment instrument comprising:
a rotating body that extends along a longitudinal axis from a proximal end to a distal end and includes an end effector on the distal end, the rotating body including a connecting portion;
a housing that is configured to support the rotating body such that the rotating body is rotatable around a predetermined rotation axis with respect to the housing; and
a lock mechanism that is configured to prevent the rotating body from rotating around the predetermined rotation axis when the longitudinal axis of the rotating body deviates from the predetermined rotation axis,
wherein:
one of the connecting portion and the housing includes an engagement projection that protrudes in a direction transverse to the predetermined rotation axis, and a different one of the connecting portion and the housing includes an engagement recess that is recessed in the direction transverse to the predetermined rotation axis and extends entirely around the predetermined rotation axis,
the engagement projection and the engagement recess form a joint assembly that connects the rotating body to the housing,
the engagement projection is configured to rotate around the predetermined rotation axis relative to the engagement recess in a state in which the engagement projection is disposed in the engagement recess,
the lock mechanism is formed by a first sliding resistance surface of the engagement projection and a second sliding resistance surface of the engagement recess that is configured to engage the first sliding resistance surface to prevent the rotation of the rotating body around the predetermined rotation axis when the longitudinal axis of the rotating body deviates from the predetermined rotation axis, and
the engagement projection and the engagement recess further include rotation support surfaces that are:
parallel to the longitudinal axis in a state in which the longitudinal axis is not deviated from the predetermined rotation axis, and
formed of a material that suppresses generation of a frictional force when the rotation support surfaces are in contact with each other or are subjected to surface processing that suppresses the generation of a frictional force when the rotation support surfaces are in contact with each other.

17. The treatment instrument according to claim 16, wherein:
the rotation support surfaces include:
a first rotation support surface of the engagement projection, and
a second rotation support surface of the engagement recess,
the second rotation support surface faces the first rotation support surface, and
the first sliding resistance surface is configured to come into contact with the second sliding resistance surface to generate a frictional force larger than a frictional force generated between the first rotation support surface and the second rotation support surface when the first rotation support surface and the second rotation support surface come into contact with each other.

18. The treatment instrument according to claim 16, wherein the first sliding resistance surface and the second sliding resistance surface are transverse to the longitudinal axis in the state in which the longitudinal axis is not deviated from the predetermined rotation axis.

* * * * *